(12) United States Patent
Gidwani et al.

(10) Patent No.: US 8,766,005 B2
(45) Date of Patent: Jul. 1, 2014

(54) PROCESS FOR PRODUCING FINGOLIMOD SALTS

(75) Inventors: Ramesh Matioram Gidwani, Mumbai (IN); Channaveerayya Hiremath, Mumbai (IN)

(73) Assignee: Ratiopharm GmbH, Ulm (DE)

( * ) Notice: Subject to any disclaimer, the term of this patent is extended or adjusted under 35 U.S.C. 154(b) by 0 days.

(21) Appl. No.: 13/386,808

(22) PCT Filed: Jul. 23, 2010

(86) PCT No.: PCT/EP2010/004547
§ 371 (c)(1),
(2), (4) Date: Apr. 3, 2012

(87) PCT Pub. No.: WO2011/009634
PCT Pub. Date: Jan. 27, 2011

(65) Prior Publication Data
US 2012/0184617 A1    Jul. 19, 2012

(30) Foreign Application Priority Data
Jul. 24, 2009  (IN) ............................ 1535/DEL/2009

(51) Int. Cl.
C07C 215/28  (2006.01)
C07C 213/02  (2006.01)
A61K 31/14  (2006.01)

(52) U.S. Cl.
USPC .......................................... 564/285; 514/643

(58) Field of Classification Search
None
See application file for complete search history.

(56) References Cited

U.S. PATENT DOCUMENTS 6,476,004 B1   11/2002   Sakai et al.

FOREIGN PATENT DOCUMENTS

| CN | 1814583 A | 8/2006 |
|---|---|---|
| EP | 0627406 A1 | 12/1994 |
| EP | 0 812 588 A1 | 12/1997 |
| JP | 11-310556 A | 11/1999 |
| WO | WO 03/097028 A1 | 11/2003 |
| WO | WO 2007/041368 A2 | 4/2007 |
| WO | WO 2007/143081 A2 | 12/2007 |
| WO | WO 2009/115534 A1 | 9/2009 |
| WO | WO 2010/055027 A2 | 5/2010 |

OTHER PUBLICATIONS

*Ex parte Hauel*, Patent Trial and Appeal Board publically available final decision, Appeal No. 2011-010664, U.S. Appl. No. 10/383,198, filed Mar. 25, 2013.*
Durand et al., "A New Efficient Synthesis of the Immunosuppressive Agent FTY-720", Synthesis 2000, No. 4, pp. 505-506, ISSN 0039-7881.
Chiba, K., et al., "FTY720 Immunosuppressant 2-Amino-2-[-(4-octylphenyl)ethyl]-1,3-propanediol hydrochloride", Drugs of the Future (1997), vol. 22, No. 1, pp. 18-22.
Chino, M., et al., "An efficient total synthesis of a sphingosine-1-phosphate receptor agonist KRP-203", Tetrahedron (2008), vol. 64, No. 17, pp. 3859-3866.
Fujita, T., et al., "Potent Immunosuppressants, 2-Alkyl-2-aminopropane-1,3-diols", Journal of Medicinal Chemistry (1996), vol. 39, pp. 4451-4459.
Gould, P., "Salt selection for basic drugs", International Journal of Pharmaceutics (1986), vol. 33, pp. 201-217.
Kiuchi, M., et al., "Synthesis and Immunosuppressive Activity of 2-Substituted 2-Aminopropane-1,3-diols and 2-Aminoethanols", Journal of Medicinal Chemistry (2000), vol. 43, pp. 2946-2961.

* cited by examiner

*Primary Examiner* — Brian J Davis
(74) *Attorney, Agent, or Firm* — Baker & Hostetler LLP

(57) ABSTRACT

The invention relates to a process for producing pharmaceutically acceptable salts of fingolimod (I), comprising the step of reacting N-[1,1-bis hydroxymethyl-3-(4-octyl phenyl)-propyl]-acylamide (II) with an acidic compound. Furthermore, the invention provides different pharmaceutically acceptable salts of fingolimod and a polymorphic form of fingolimod hydrochloride.

18 Claims, 23 Drawing Sheets

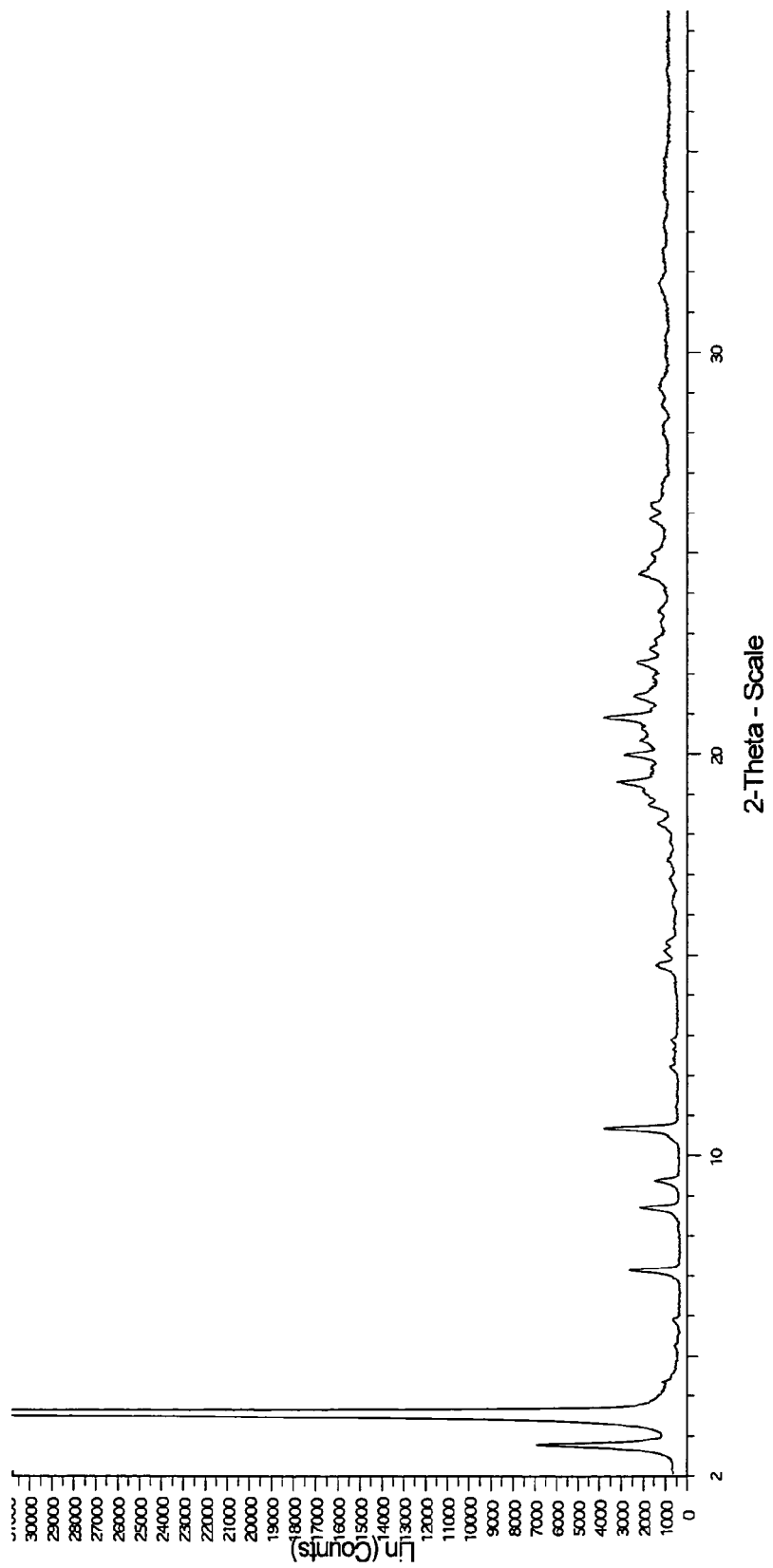
Figure 1: XRPD of Fingolimod hydrochloride as obtained by Example 2

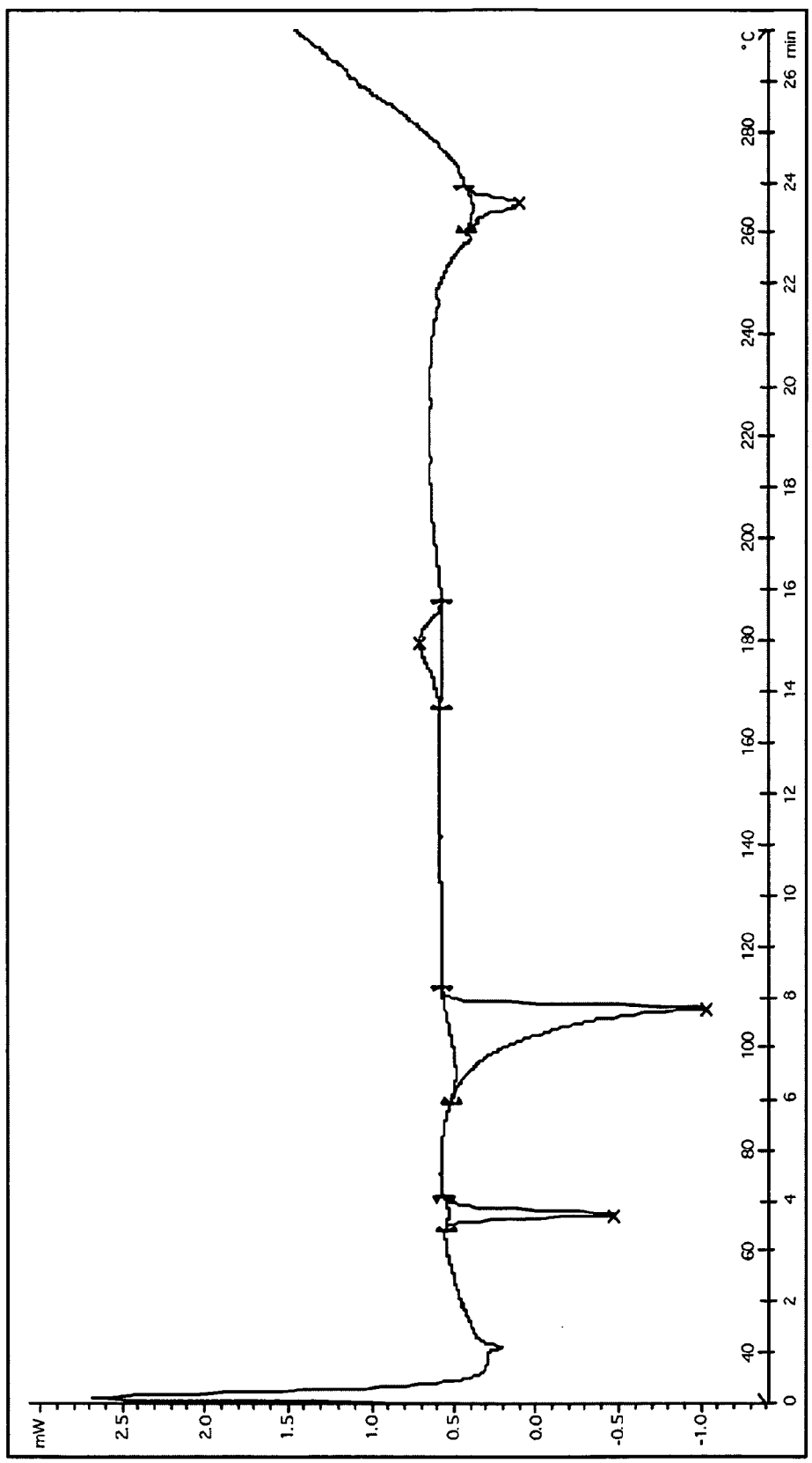
Figure 2: DSC of Fingolimod hydrochloride as obtained by Example 2

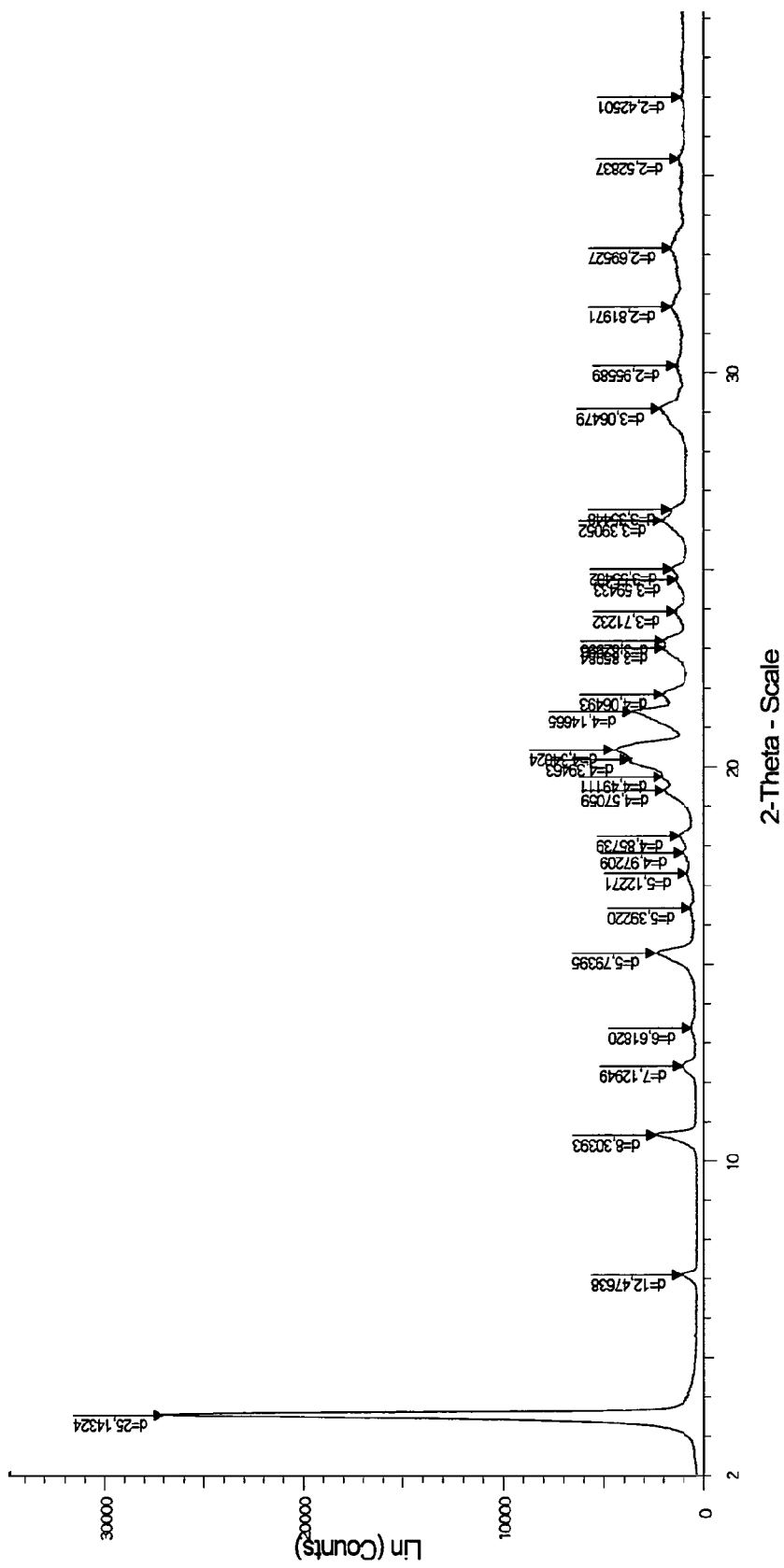
Figure 3: XRPD of Fingolimod hydrochloride as obtained by Example 4 (freeze-drying)

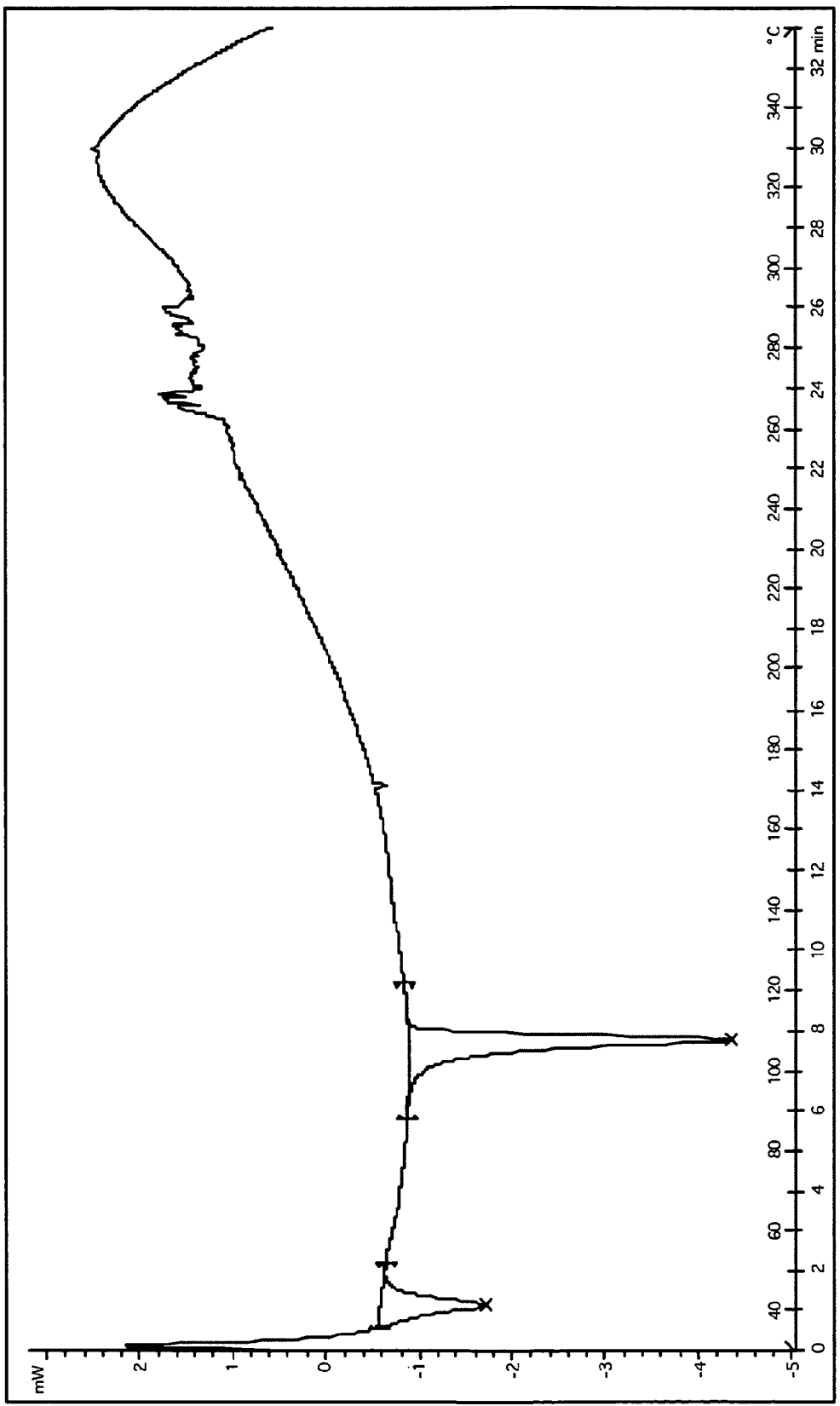
Figure 4: DSC of Fingolimod hydrochloride as obtained in Example 4 (freeze-drying)

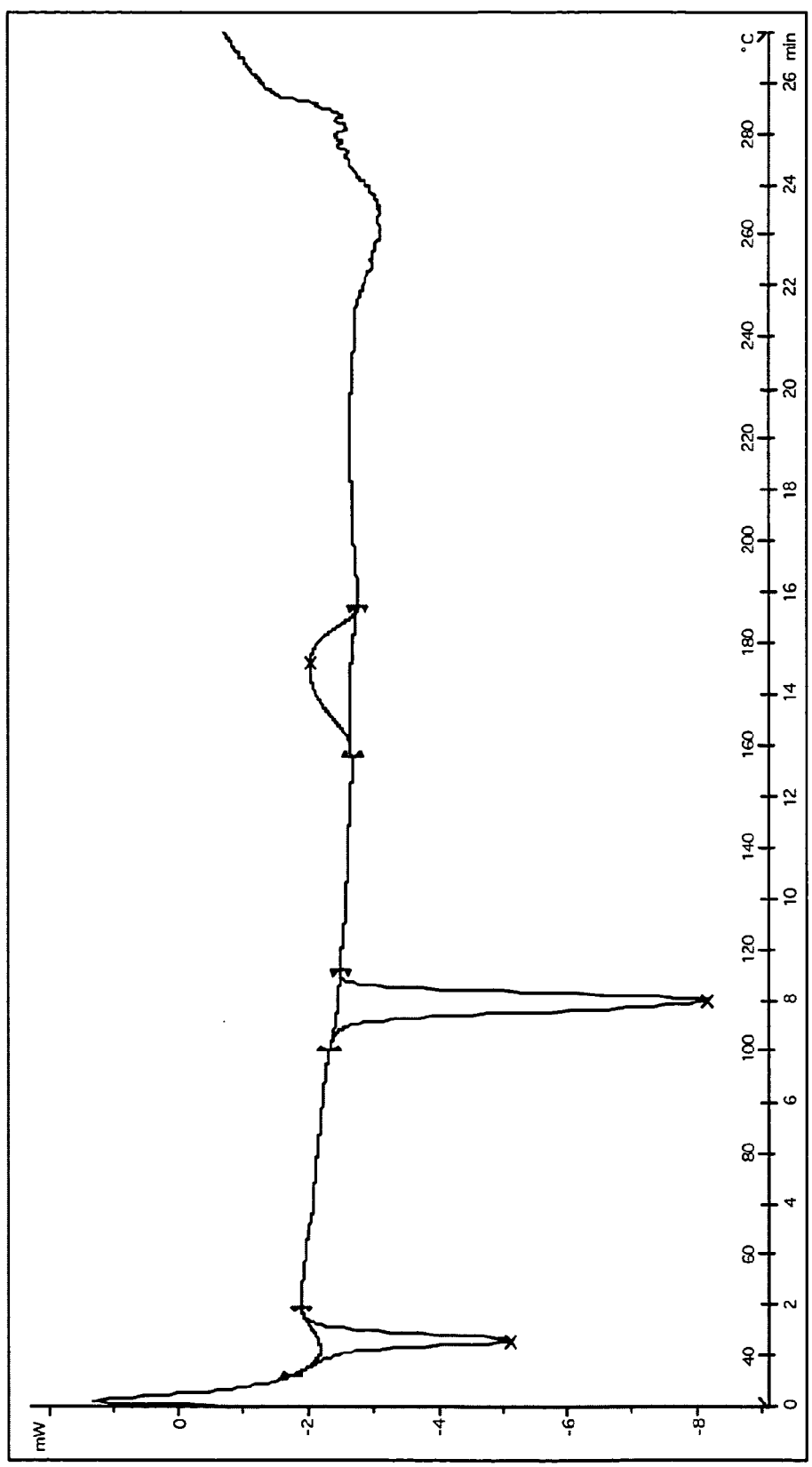
Figure 5: DSC of Fingolimod hydrochloride as obtained in Example 6 (milling)

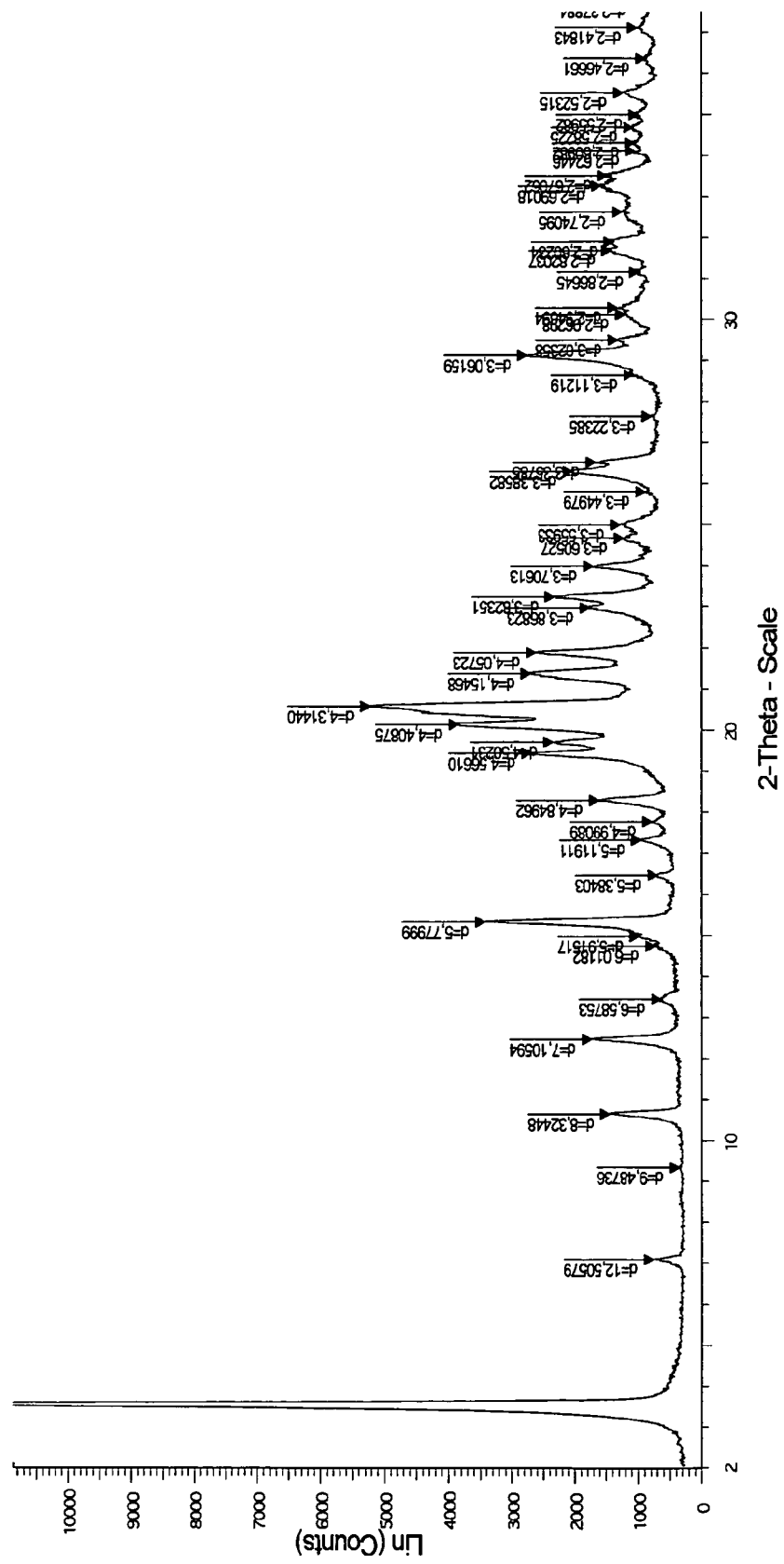
Figure 6: XRPD of Fingolimod hydrochloride as obtained in Example 6 (milling)

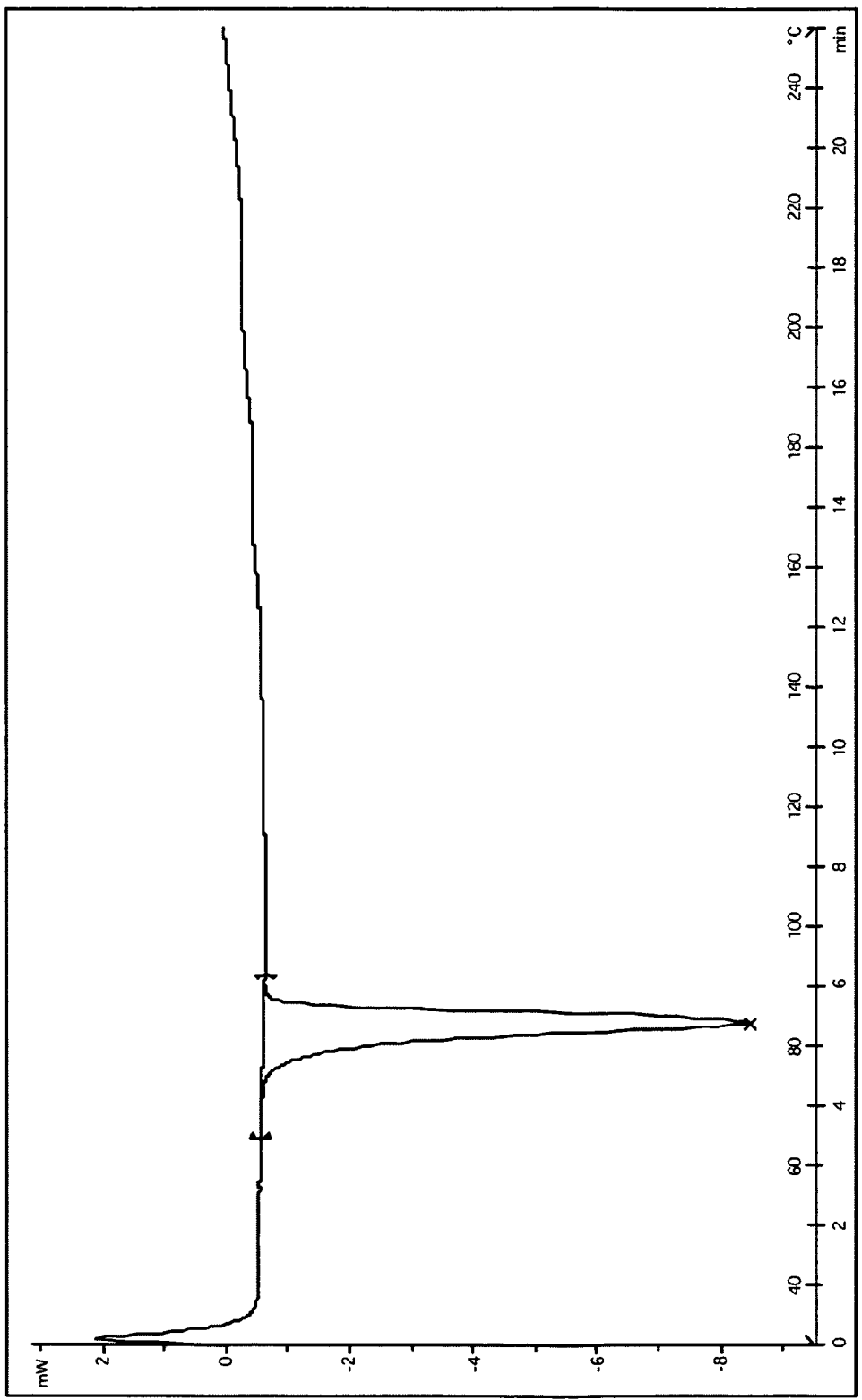
Figure 7: DSC of Fingolimod hydrobromide as obtained in Example 7

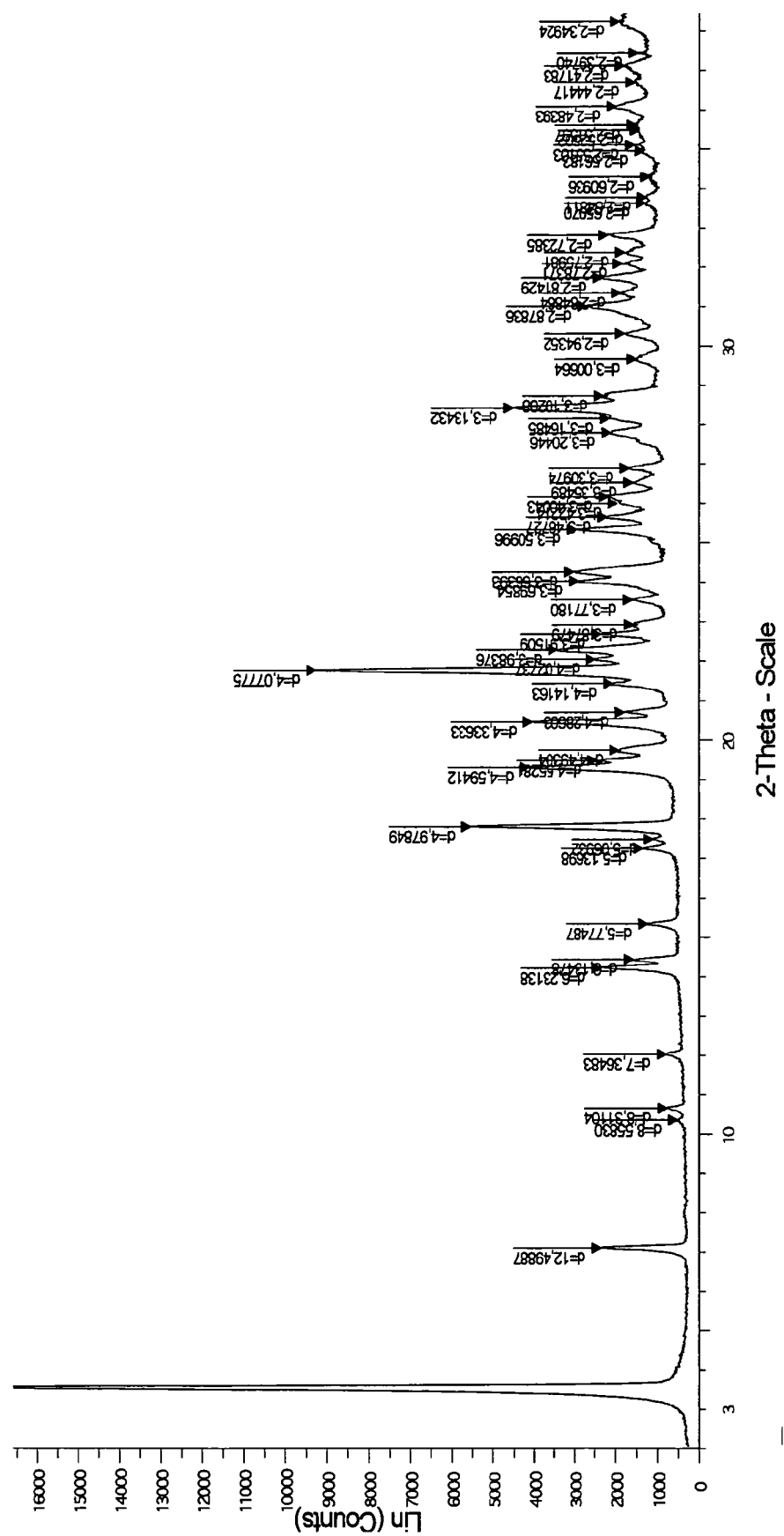
Figure 8: XRPD of Fingolimod hydrobromide as obtained in Example 7

Figure 9: DSC of Fingolimod succinate as obtained by Example 8
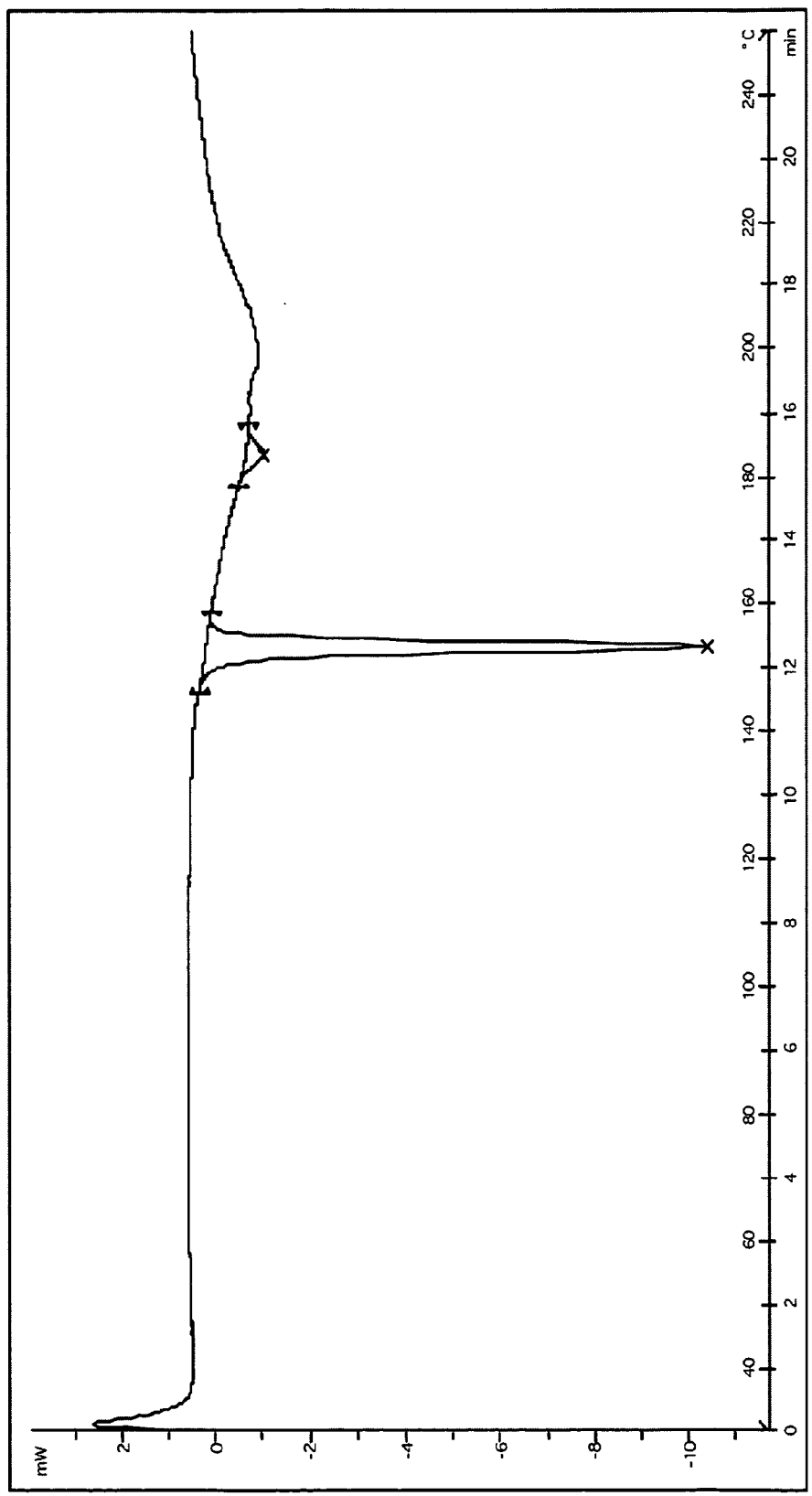

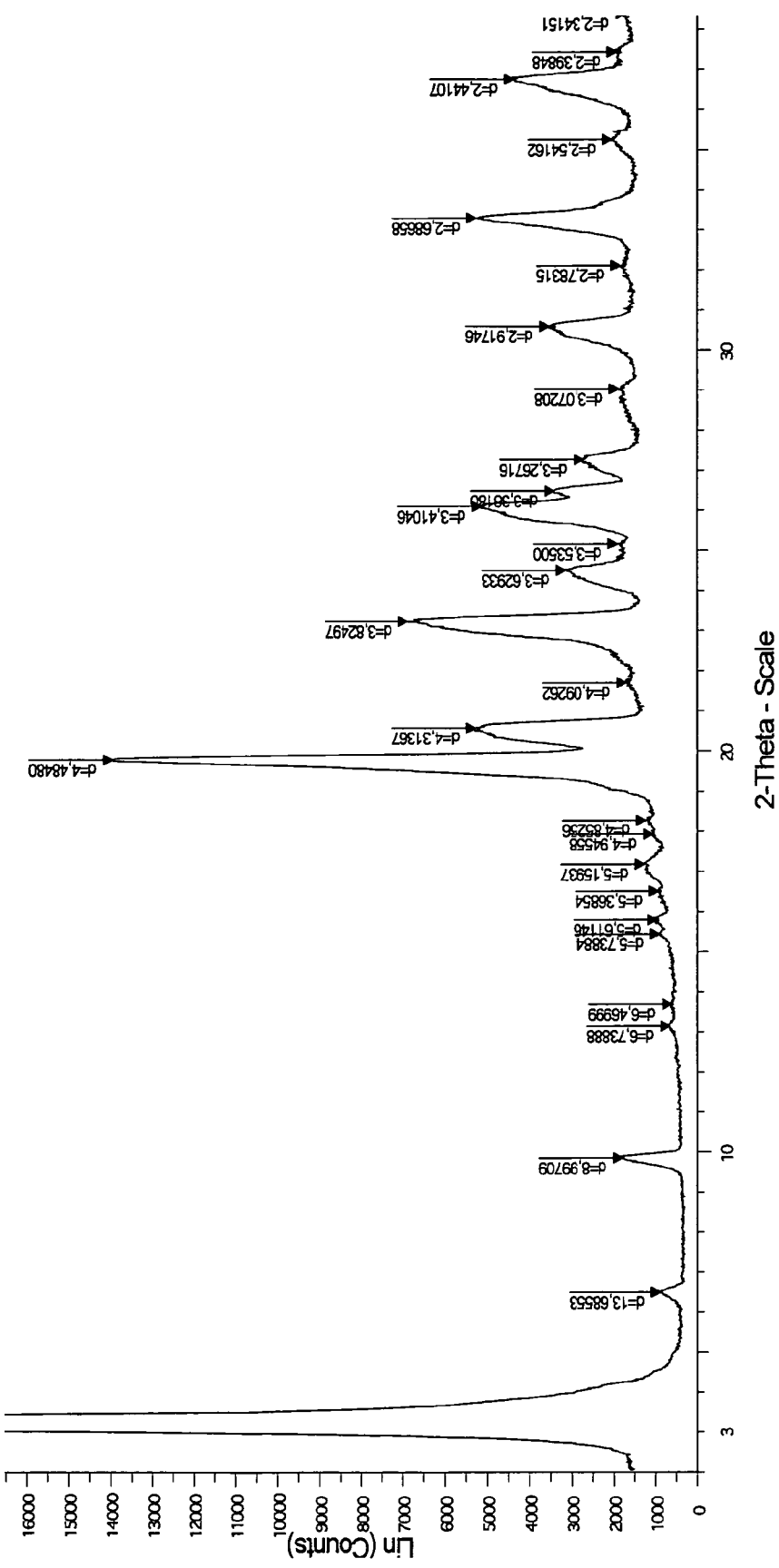
Figure 10: XRPD of Fingolimod succinate as obtained by Example 8

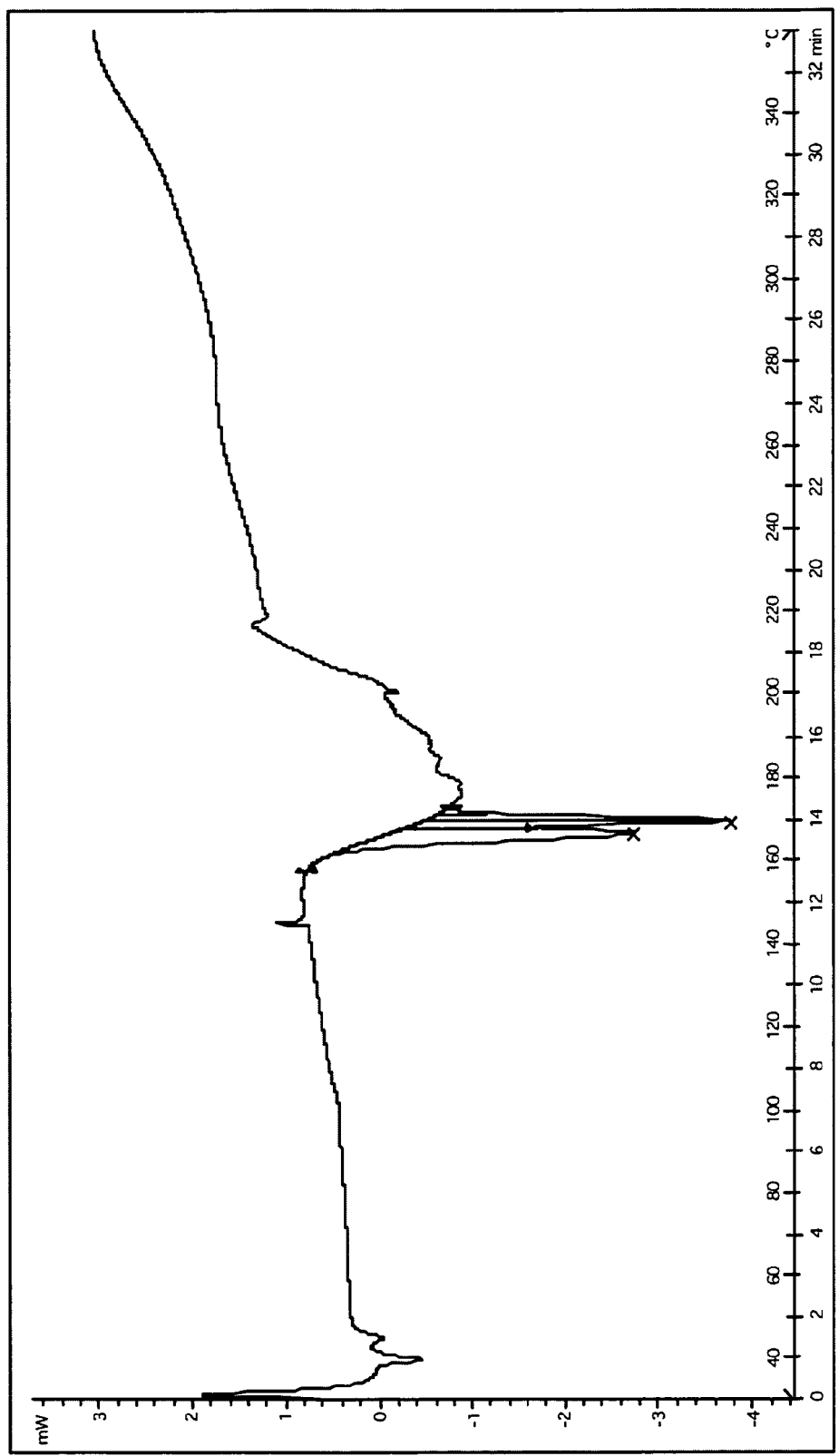
Figure 11:  DSC of Fingolimod oxalate as obtained by Example 8:

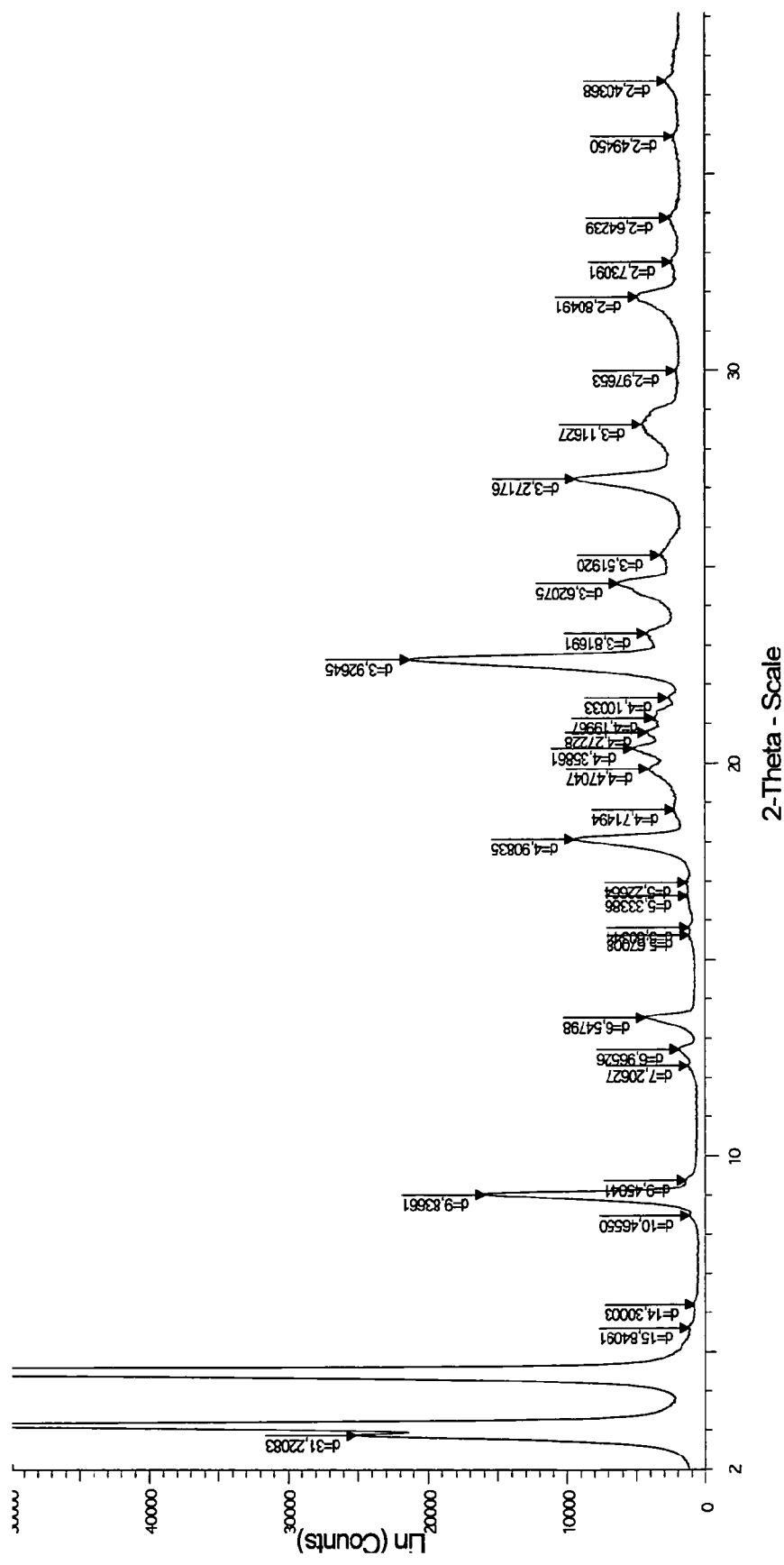
Figure 12: XRPD of Fingolimod oxalate as obtained by Example 8

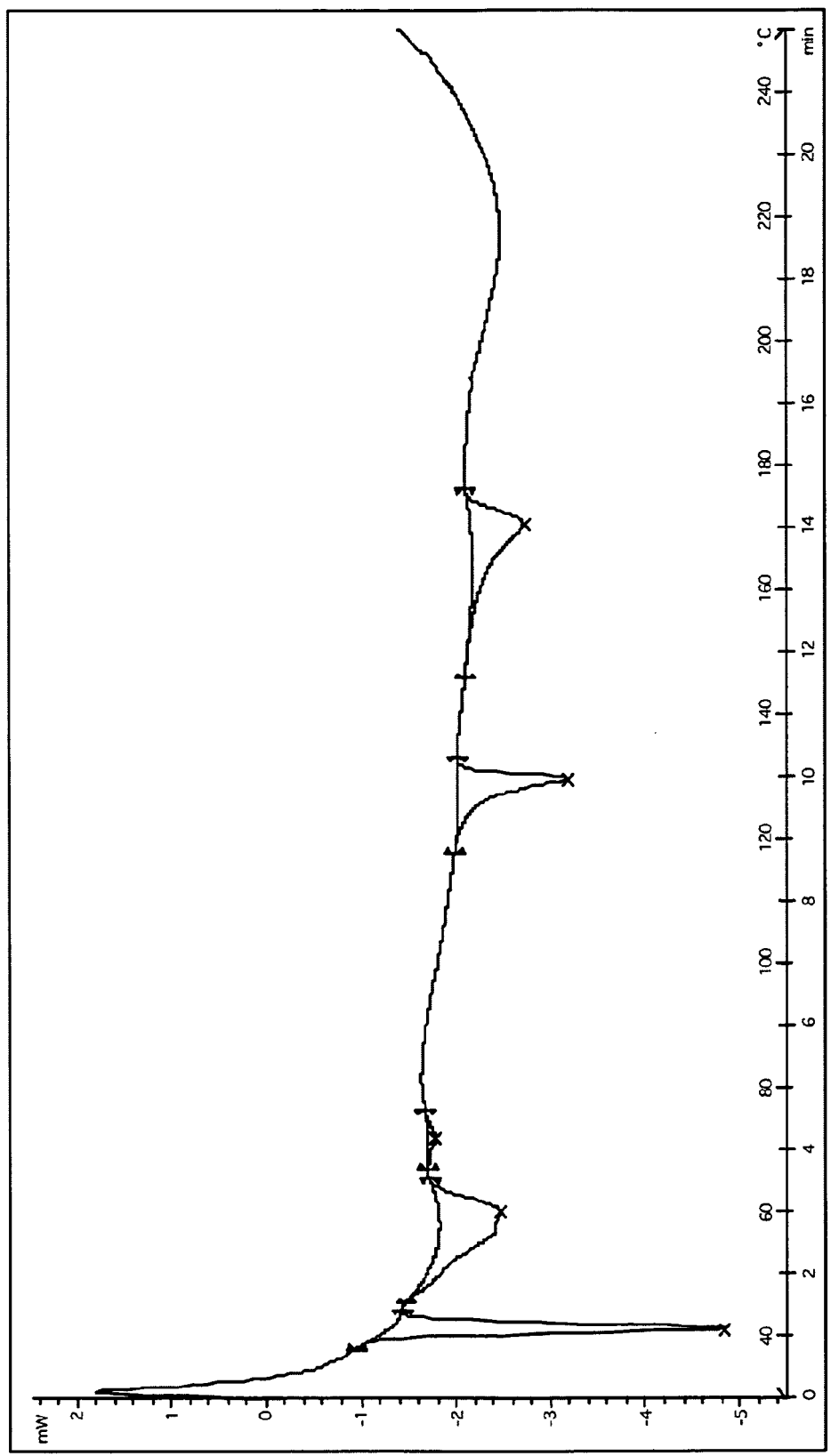
Figure 13: DSC of Fingolimod phosphate as obtained by Example 8

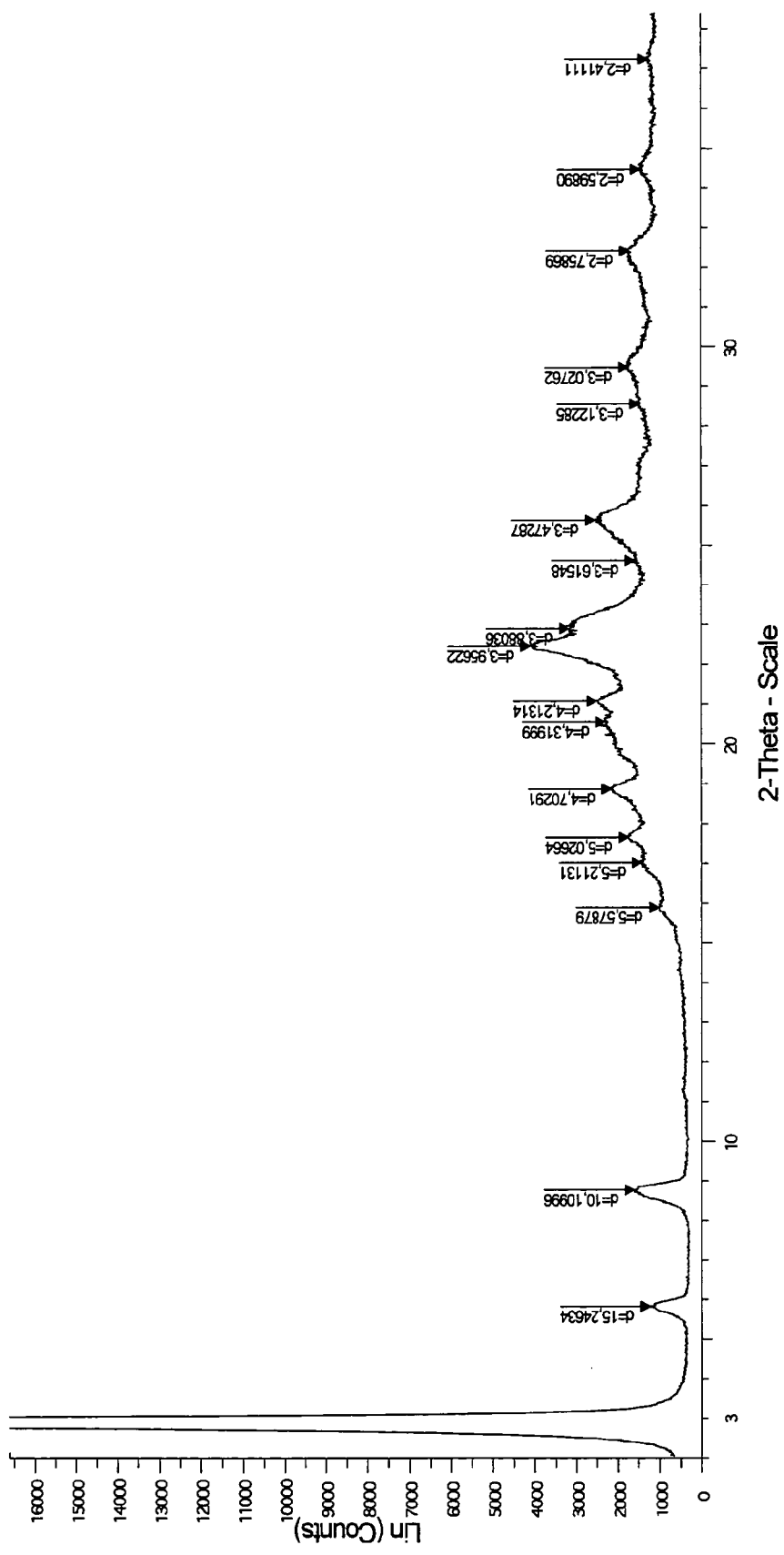
Figure 14: XRPD of Fingolimod phosphate as obtained by Example 8

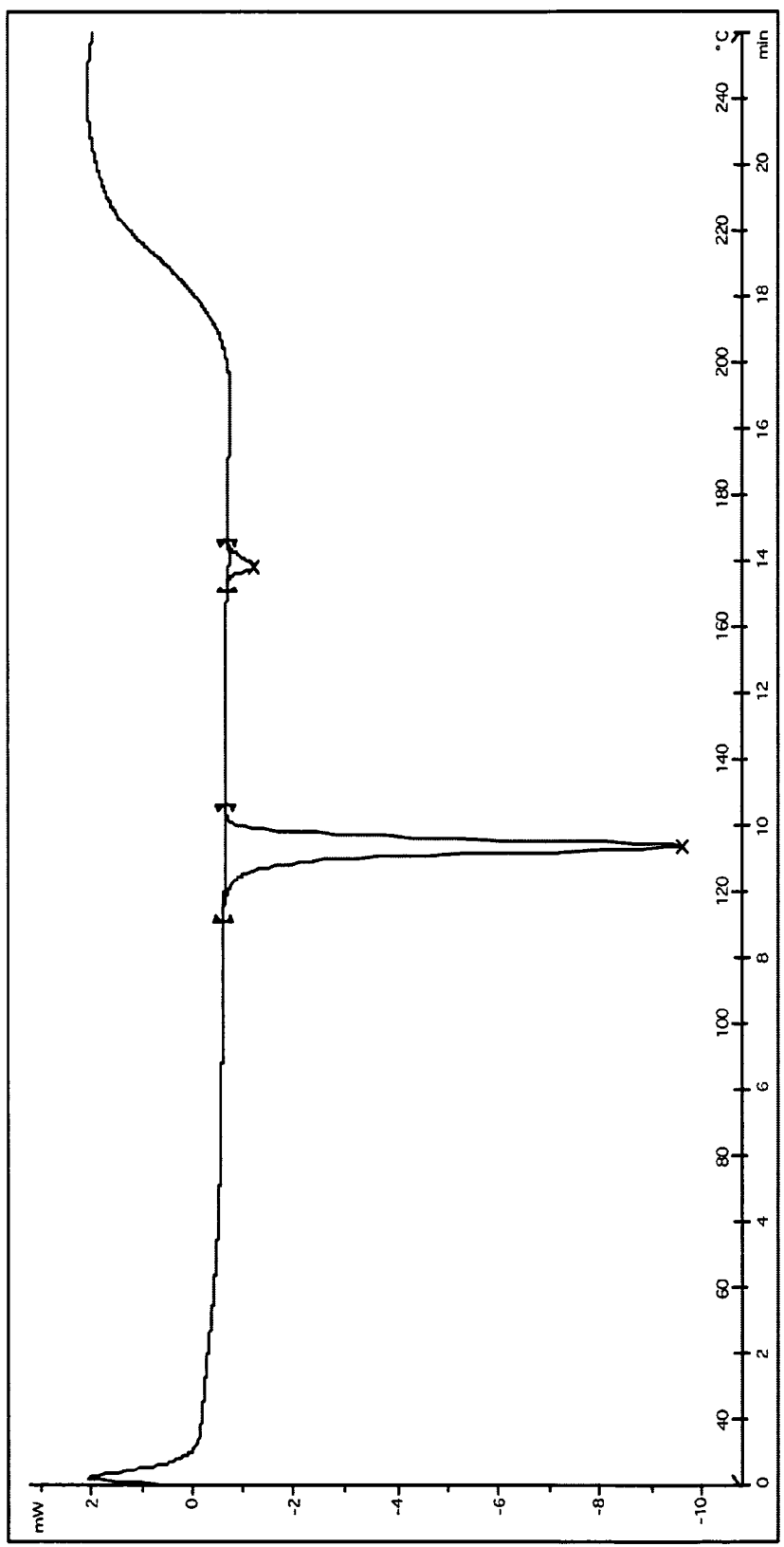
Figure 15: DSC of Fingolimod mandelate as obtained by Example 8

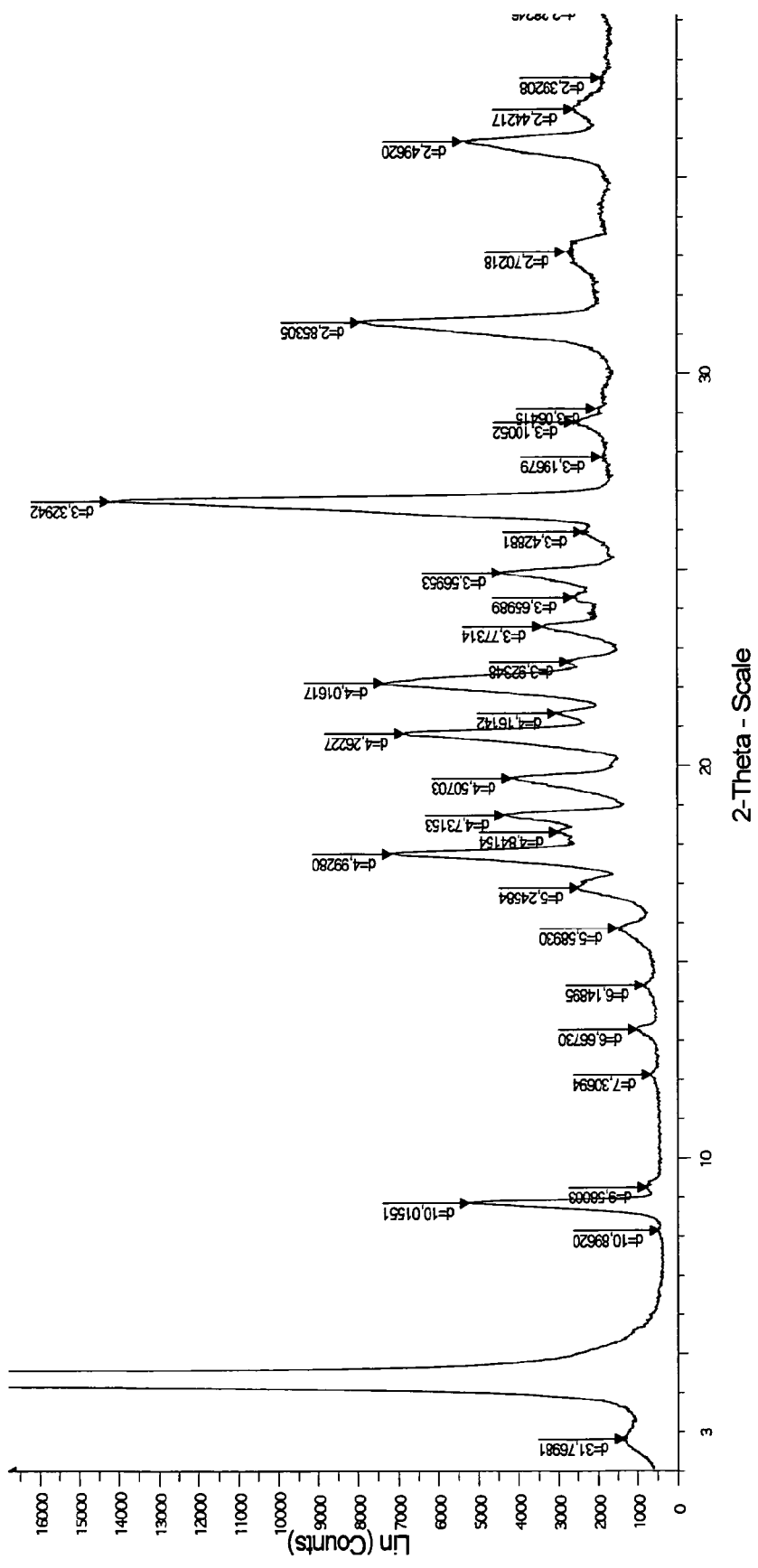
Figure 16: XRPD of Fingolimod mandelate as obtained by Example 8

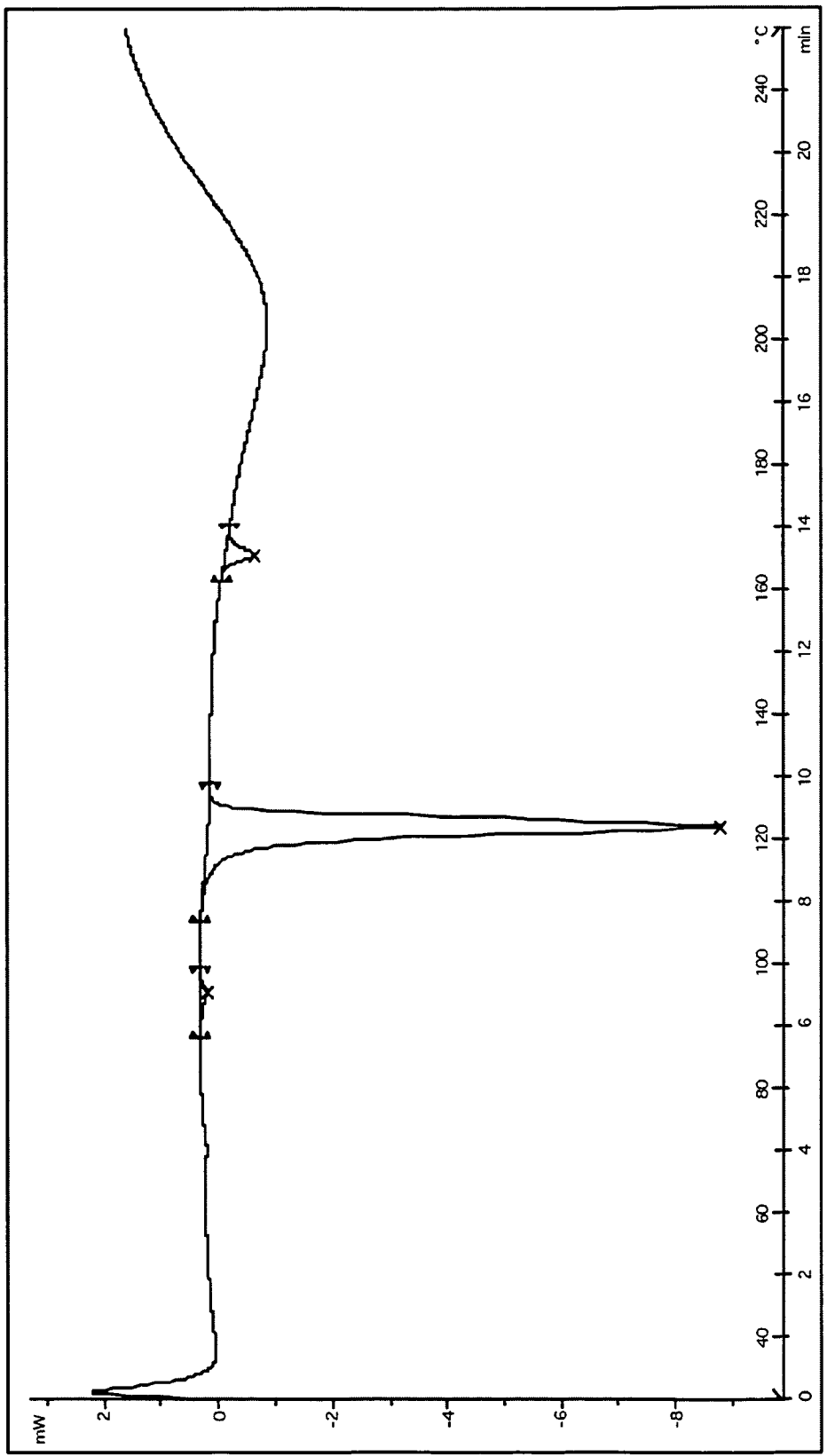
Figure 17: DSC of Fingolimod adipate as obtained by Example 8

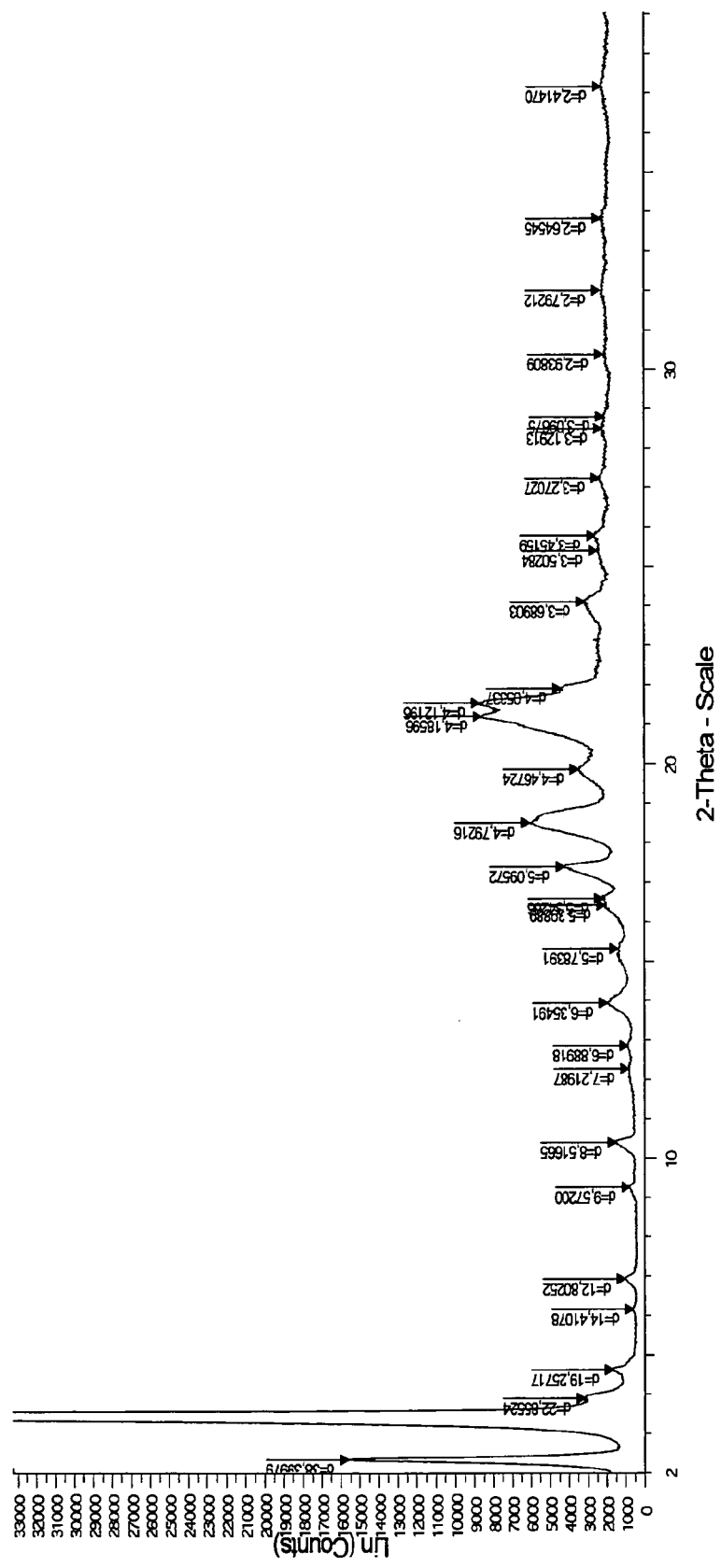
Figure 18: XRPD of Fingolimod adipate as obtained by Example 8

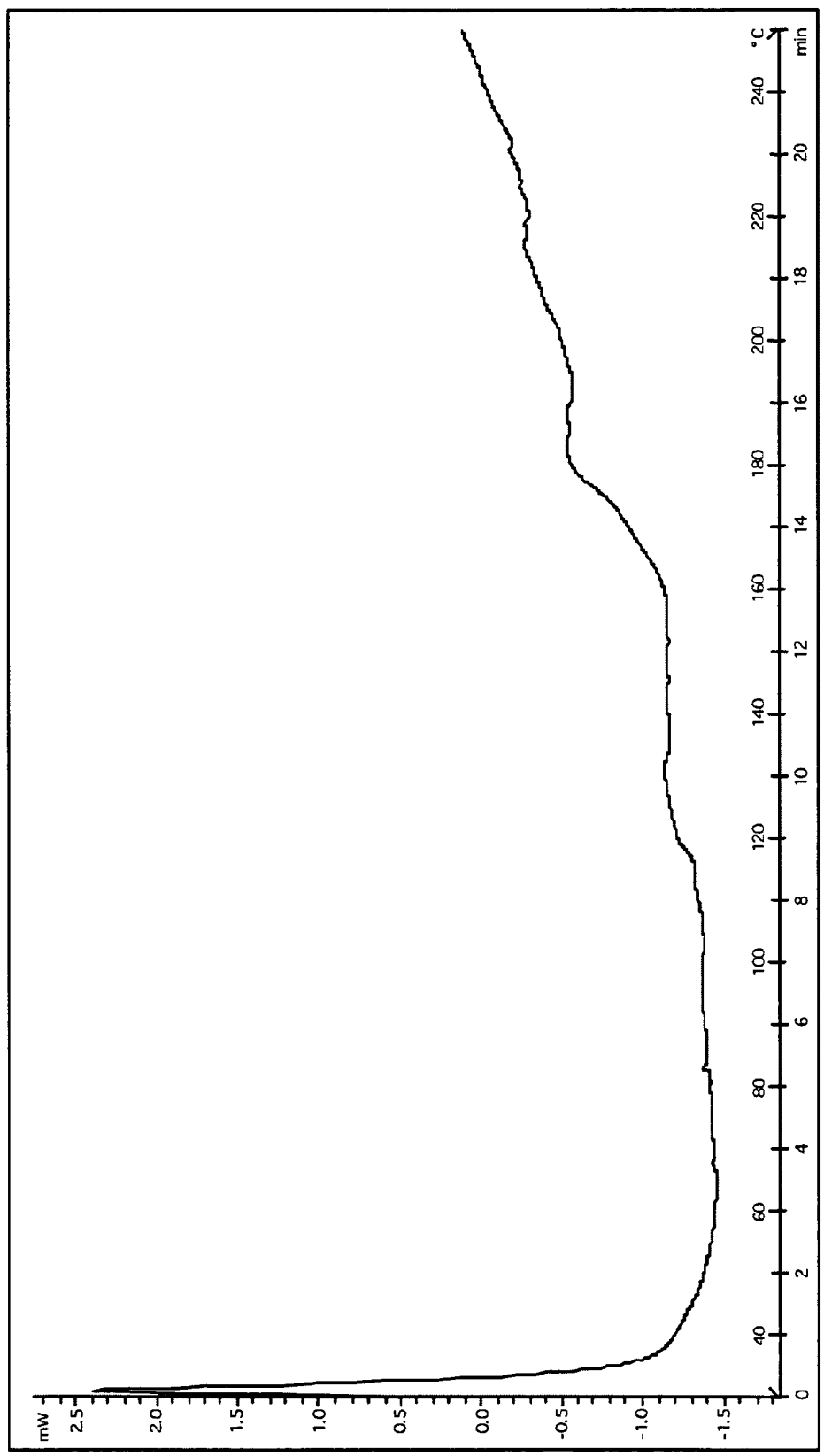
Figure 19: DSC of Fingolimod ascorbate as obtained by Example 8

Figure 20: DSC of Fingolimod sulfate I as obtained by Example 8:
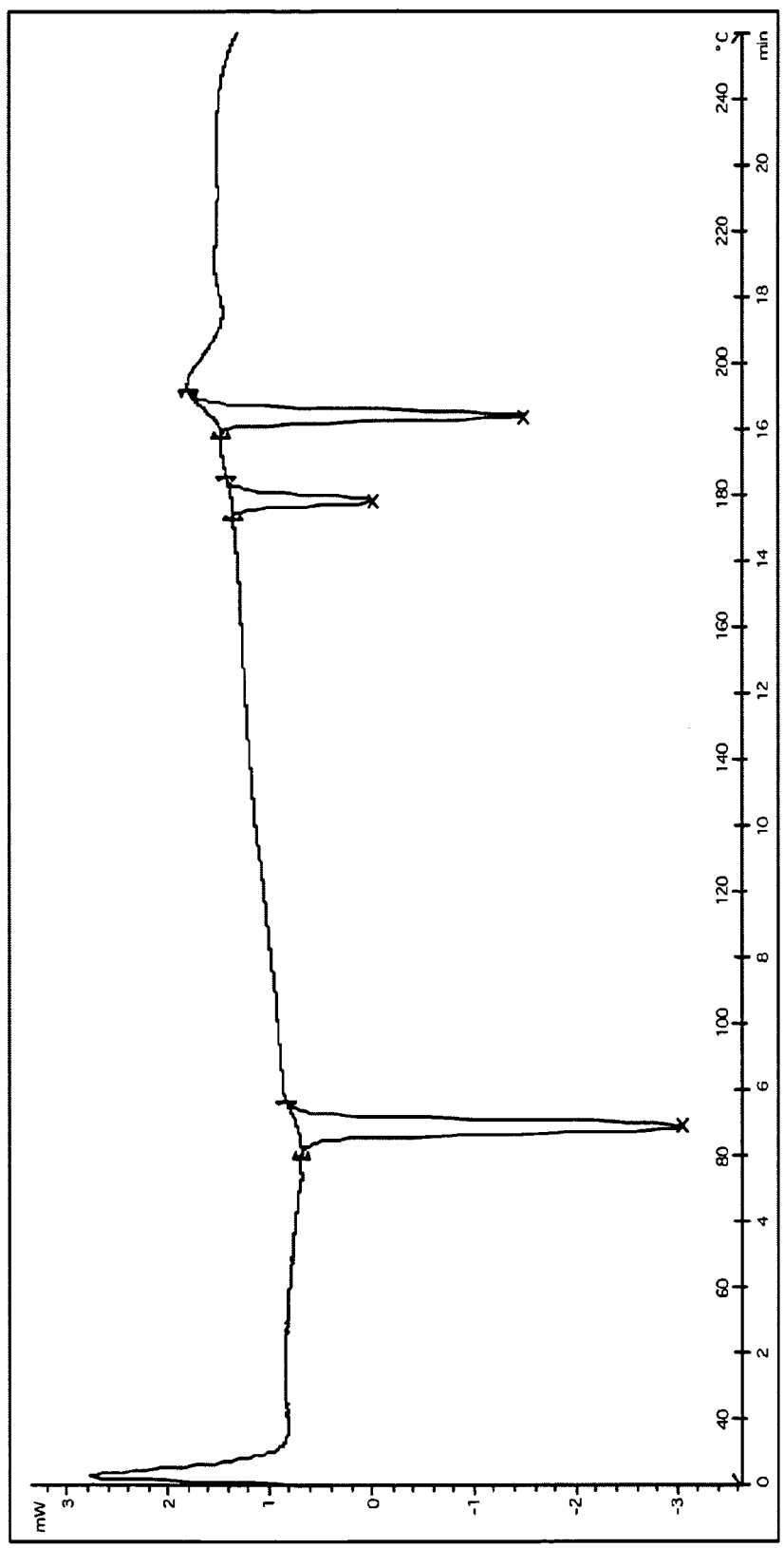

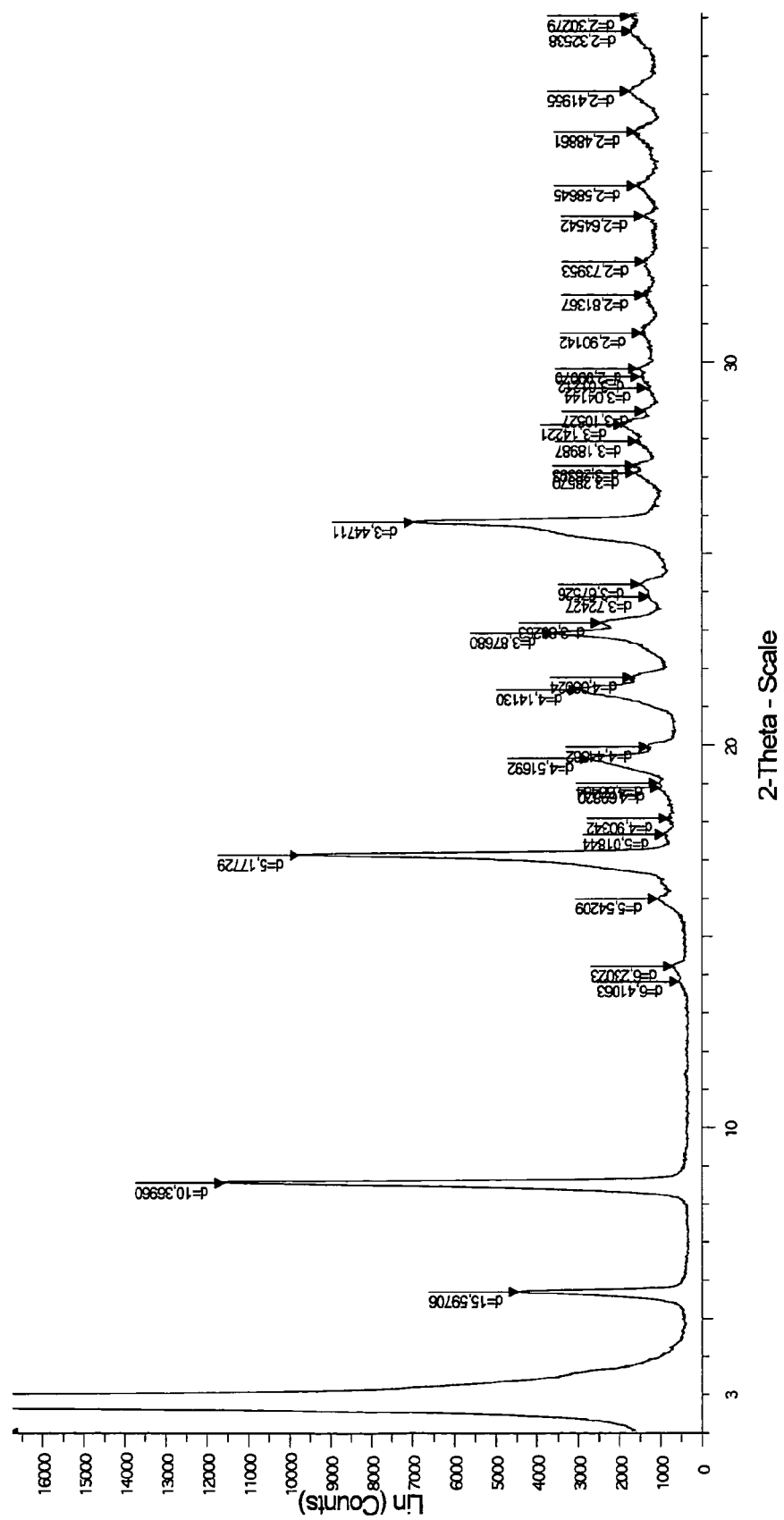
Figure 21: XRPD of Fingolimod sulfate I as obtained in Example 8

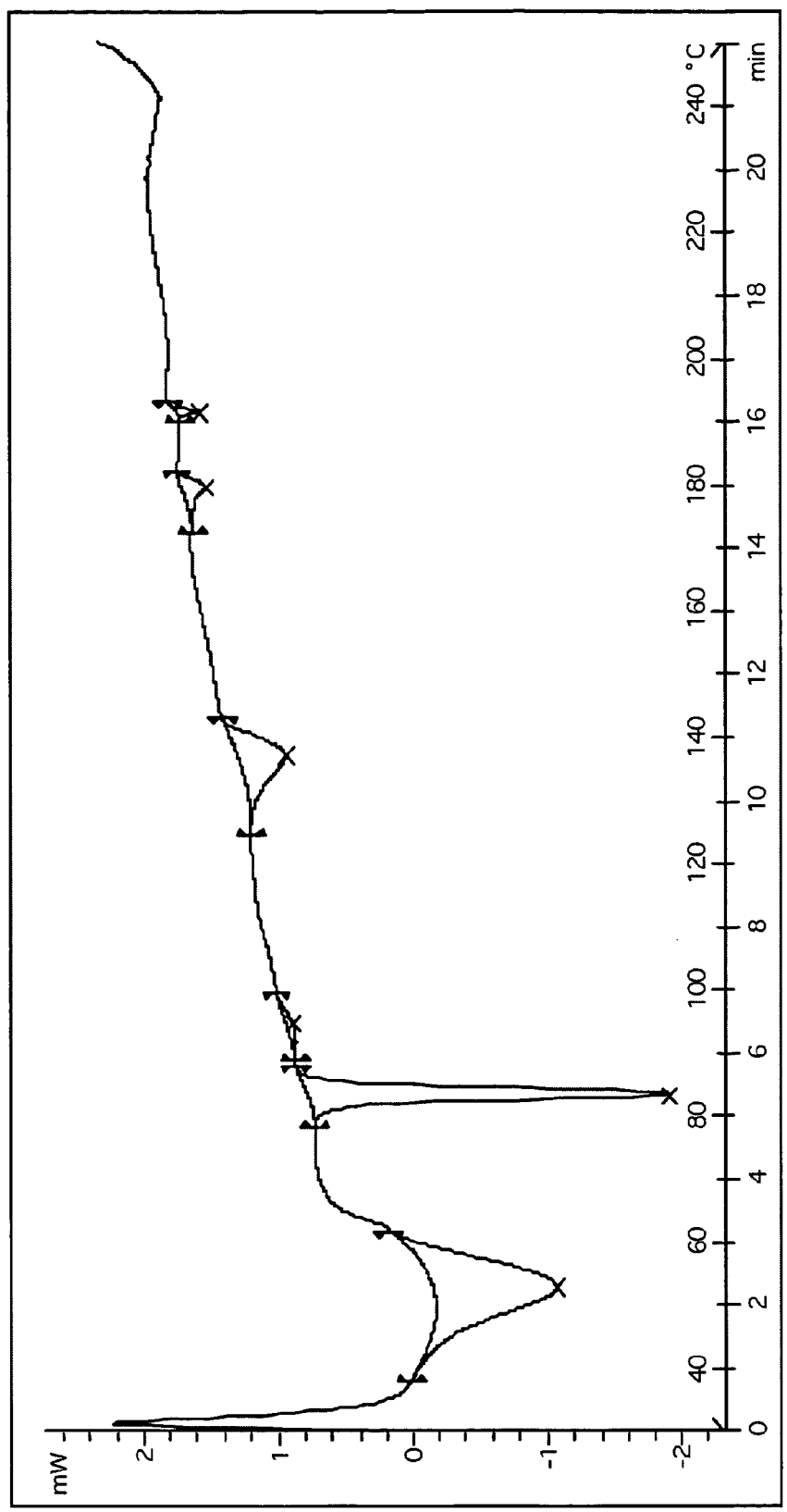
Figure 22: DSC of Fingolimod sulfate II as obtained in Example 8:

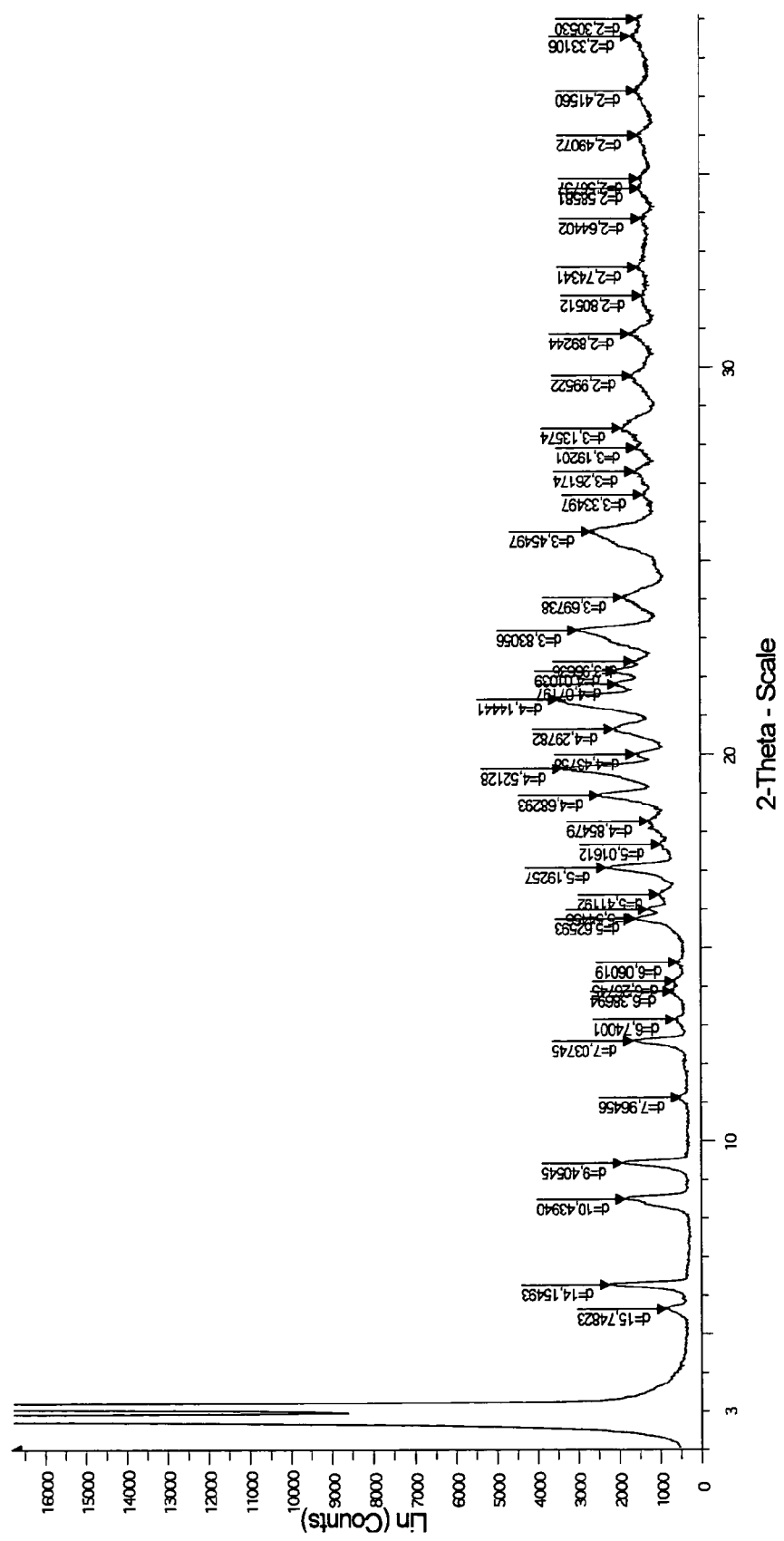
Figure 23: XRPD of Fingolimod sulfate II

PROCESS FOR PRODUCING FINGOLIMOD SALTS

CROSS-REFERENCE TO RELATED APPLICATIONS

This application is a U.S. national phase filed under 35 U.S.C. §371 of International Application No. PCT/EP2010/004547 filed on Jul. 23, 2010, which claims priority to Indian Application No. 1535/DEL/2009 filed on Jul. 24, 2009, the contents of which are incorporated herein by reference in their entirety.

The invention relates to a process for producing pharmaceutically acceptable salts of fingolimod (Ib), comprising the step of reacting a N-[1,1-bis hydroxymethyl-3-(4-octyl phenyl)-propyl]-acylamide (II) with an acidic compound. Furthermore, the invention provides different pharmaceutically acceptable salts of fingolimod and a desirable polymorphic form of fingolimod hydrochloride.

Fingolimod is a known immunosuppressant drug that causes lymphopenia by preventing egress of lymphocytes from lymph nodes. It is expected that fingolimod can be used as monotherapy for relapsing-remitting multiple sclerosis.

The chemical name of fingolimod (in form of the free base) is (2-amino-2-[2-(4-octyl phenyl)-ethyl]-propane-1,3-diol). It is illustrated by the chemical formula (Ib)

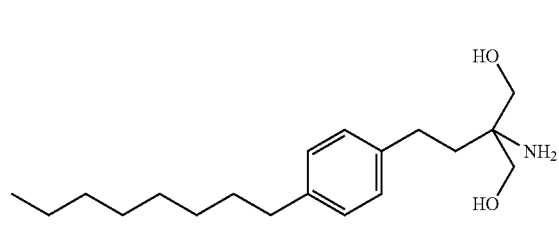

A process for preparing fingolimod is disclosed in Example 28 of EP 0 627 406 B 1. The process comprises eight steps. Steps 7 and 8 (=step 7b) comprise the following reactions:

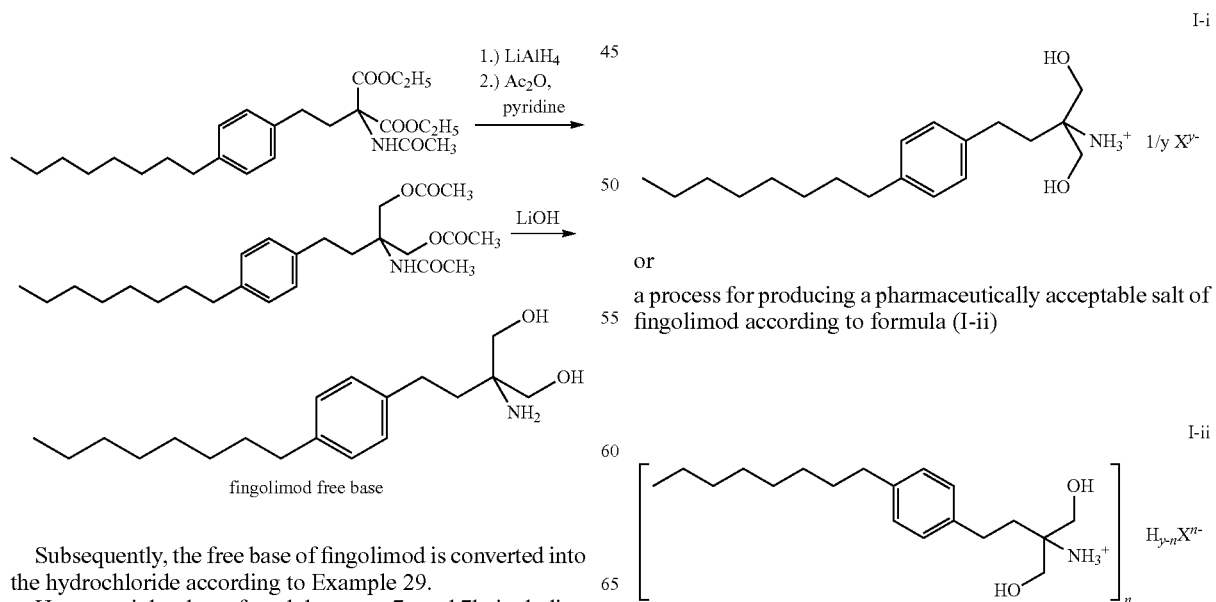

Subsequently, the free base of fingolimod is converted into the hydrochloride according to Example 29.

However, it has been found that steps 7a and 7b, including the subsequent conversion into the salt, can be carried out only with low yield (about 26%). Furthermore, the above process requires pyridine as solvent, which is undesirable due to toxic effects. In addition, the process according to EP 0 627 406 requires anhydrous THF (tetrahydrofurane), a large excess of LiOH and an isolation step using column chromatography, which is not desirable from an economic point of view.

The process according to Example 28 was improved by Durand et al., see "A new Efficient Synthesis of the Immunosuppressive Agent FTY-720", Synthesis 2000, No. 4, 505-506. Durand et al. disclosed an improved process for steps 1 to 6. However, Durand et al. were not able to improve steps 7a and 7b, including the subsequent conversion into the hydrochloric salt. Therefore, when following the synthesis concept according to Durand at al., the resulting process still shows deficiencies with regard to yield, undesirable solvents and purity.

Therefore, it was an object of the present invention to provide an improved process for producing pharmaceutically acceptable salts of fingolimod. In particular, the process should be carried out in high yield and should enable a production in large scale. It was a further object of the present invention to provide a process for producing fingolimod having a high degree of purity and a low residual solvent content. The use of solvents, having undesirable toxic effects, should be avoided. Moreover, it was an object of the present invention to provide an improved process for producing not only fingolimod in form of the hydrochloride salt but fingolimod in form of a variety of different pharmaceutically acceptable salts. In addition, it was an object of the present invention to provide fingolimod in form of pharmaceutically acceptable salts, showing a constant dissolution profile before and after storage.

The above mentioned objects have been unexpectedly solved by reacting N-[1,1-bis hydroxymethyl-3-(4-octyl phenyl)-propyl]-acylamide (II) with an acidic compound.

Hence, a subject of the present invention is a process for producing a pharmaceutically acceptable salt of fingolimod according to formula (I-i)

or a process for producing a pharmaceutically acceptable salt of fingolimod according to formula (I-ii)

said process comprising reacting a compound according to formula (II)

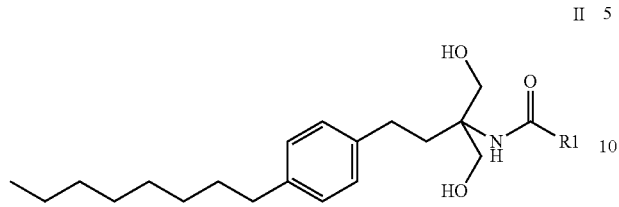

with an acidic compound of the formula $H_y X$,
wherein in the above formulae H is a dissociable hydrogen atom, X is a pharmaceutically acceptable residue, y and n are a natural number from 1 to 5, preferably from 1 to 3, wherein n≤y and $R_1$ is an organic residue, preferably an alkyl or aryl group, more preferably methyl. In a possible embodiment of formula (I-ii) n is smaller than y (n<y).

Formula (I-i) corresponds to formula (I-ii) if y=n.

In addition, further subjects of the present invention are compounds according to formula (I-i) or (I-ii), wherein X is ascorbate, succinate, oxalate, phosphate, mandelate, adipate, ethanesulfonate, naphthalene-1,5-disulfonate, naphthalene-1-sulfonate, naphthalene-2-sulfonate, L-aspartate, 4-acetamidobenzoate, (+) camphorate, (+) camphor-10-sulfonate, decanoate, hexanoate, octanoate, cinnamate, dodecylsulfate, ethane-1,2-disulfonate, 2-hydroxyethanesulfonate, glutarate, DL-lactate, 1-hydroxy-2-naphthoate, laureate, salicylate, tartrate, mesylate, citrate, benzoate or mixtures thereof. Moreover, further subject of the present invention are polymorphic forms of fingolimod hydrochloride.

Finally, a further subject of the present invention is the use of a chemoselective reducing agent in a process for producing a pharmaceutically acceptable salt of fingolimod, wherein fingolimod in form of the free base does not occur as an intermediate in said process.

BRIEF DESCRIPTION OF THE DRAWINGS

FIG. 1 depicts an X-ray powder diffractogram (XRPD) of fingolimod hydrochloride as obtained by Example 2.

FIG. 2 depicts a differential scanning colorimetry thermogram (DSC) of Fingolimod hydrochloride as obtained by Example 2.

FIG. 3 depicts an XRPD of Finolimod hydrochloride as obtained by Example 4 (freeze-drying).

FIG. 4 depicts a DSC of Finolimod hydrochloride as obtained in Example 4 (freeze-drying).

FIG. 5 depicts a DSC of Fingolimod hydrochloride as obtained in Example 6 (milling).

FIG. 6 depicts an XRPD of Fingolimod hydrochloride as obtained in Example 6 (milling).

FIG. 7 depicts a DSC of Fingolimod hydrobromide as obtained in Example 7.

FIG. 8 depicts an XRPD of Fingolimod hydrobromide as obtained in Example 7.

FIG. 9 depicts a DSC of Fingolimod succinate as obtained by Example 8.

FIG. 10 depicts an XRPD of Fingolimod succinate as obtained by Example 8.

FIG. 11 depicts a DSC of Fingolimod oxalate as obtained by Example 8.

FIG. 12 depicts an XPRD of Fingolimod oxalate as obtained by Example 8.

FIG. 13 depicts a DSC of Fingolimod phosphate as obtained by Example 8.

FIG. 14 depicts an XRPD of Fingolimod phosphate as obtained by Example 8.

FIG. 15 depicts a DSC of Fingolimod mandelate as obtained by Example 8.

FIG. 16 depicts an XRPD of Fingolimod mandelate as obtained by Example 8.

FIG. 17 depicts a DSC of Fingolimod adipate as obtained by Example 8.

FIG. 18 depicts an XRPD of Fingolimod adipate as obtained by Example 8.

FIG. 19 depicts a DSC of Fingolimod ascorbate as obtained by Example 8.

FIG. 20 depicts a DSC of Fingolimod sulfate I as obtained by Example 8.

FIG. 21 depicts an XRPD of Fingolimod sulfate I as obtained in Example 8.

FIG. 22 depicts a DSC of Fingolimod sulfate II as obtained in Example 8.

FIG. 23 depicts an XRPD of Fingolimod sulfate II.

The process of the present invention comprises reacting a compound according to formula (II)

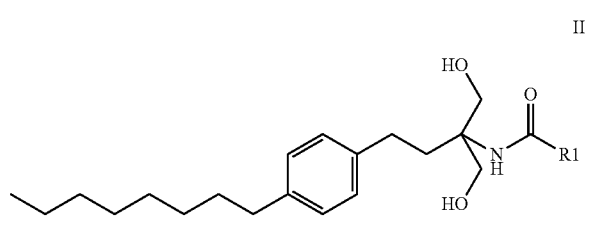

with an acidic compound.

Generally, in formula (II) $R_1$ represents an organic residue, preferably an alkyl or aryl group, more preferably a $C_1$ to $C_4$ alkyl group and, particularly, a methyl group.

In the above reaction an acidic compound is used, that means a compound being capable of dissociating protons. The acidic compound is a compound according to the formula $H_y X$, wherein H is hydrogen atom, capable of dissociating as proton. X is a pharmaceutically acceptable residue. Hence, after the proton $H^+$ has been dissociated, X is a pharmaceutically acceptable anion, preferably bromide or chloride, especially chloride, y is a natural number from 1 to 5, preferably 1 to 3, i.e. 1, 2 or 3. More preferably y is 1 or 2.

For example, if hydrochloric acid is used as acidic compound, then y is 1 and X is chloride. If oxalic acid is used as acidic compound, then y is 2 and X is oxalate.

Examples for preferred acidic compounds are hydrochloric acid, ascorbic acid, succinic acid, oxalic acid, phosphoric acid, mandelic acid, adipic acid, hydrobromic acid, sulfuric acid, acetic acid, fumaric acid, maleic acid, methane-sulfonic acid, benzenesulfonic acid. L-malic acid, ethanesulfonic acid, naphthalene-1,5-disulfonic acid, naphthalene-1-sulfonic acid, naphthalene-2-sulfonic acid, L-aspartic acid, 4-acetamidobenzoic acid, (+) camphoric acid, (+) camphor-10-sulfonic acid, decanoic acid, hexanoic acid, octanoic acid, cinnamic acid, dodecylsulfuric acid, ethane-1,2-disulfonic acid, 2-hydroxyethanesulfonic acid, glutaric acid, DL-lactic acid, 1-hydroxy-2-naphthoic acid, lauric acid, salicylic acid, tartaric acid or mixtures thereof.

In a particular preferred embodiment hydrochloric or hydrobromic acid is used as acidic compound.

The process according to the present invention results in a pharmaceutically acceptable salt of fingolimod according to formula (I-i) or (I-ii):

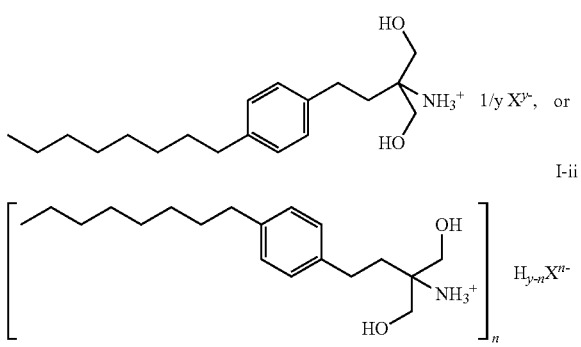

wherein y and X are defined above.

Consequently, if hydrochloric acid is used as acidic compound in formula (I-i) or (I-ii), y is 1 and X is chloride. The resulting product is fingolimod hydrochloride as illustrated in formula (Ia)

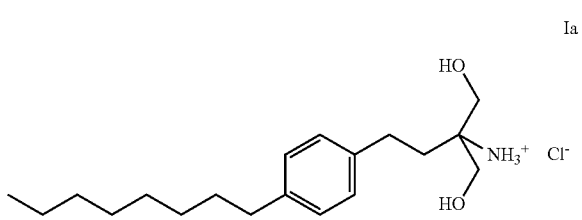 [SMILES: CCCCCCCCc1ccc(CCC([NH3+])(CO)CO)cc1 ; [Cl-]]

The reaction of the compound according to formula (II) with the acidic compound may be carried out in usual organic solvents and at usual temperatures. Preferably organic solvents, being capable of completely dissolving the acidic compound, are used. More preferably, alcohols or alcohol/water mixtures are used as suitable solvents. Particularly, an ethanol/water mixture is used.

Usually the reaction is carried out at temperatures between 10° C. and 100° C., preferably between 60° C. and 80° C. The reaction time may vary from 10 minutes to 5 hours. Usually, the reaction product (I) (=I-i or I-ii) is obtained in crystalline form.

In an embodiment of the present invention, the obtained product (I) (=I-i or I-ii) is (preferably completely) dissolved in water and/or and an organic solvent and subsequently freeze-dried. Suitable solvents are alcohols, e.g. ethanol. Preferably, water or a water/ethanol mixture is used. Freeze-drying is done, using VirTis® Bench top K Freeze dryer. The VirTis® glass bottle of 40 ml capacity, condenser temperature is from −53° C. to −105° C., particularly −104° C., and the vacuum is 15 mT (2 Pa).

In the above mentioned process a compound according to formula (II) is used. The compound according to formula (II) can be obtained by a process comprising reacting a compound according to formula (III)

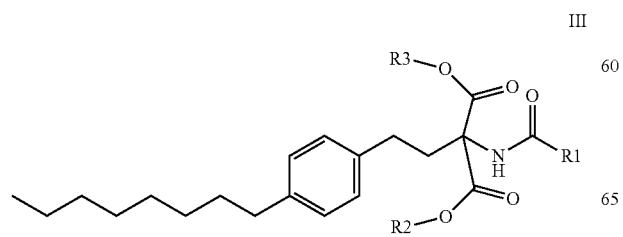

with a reducing agent, wherein in formula (III) $R_1$ is an organic residue, preferably an alkyl or aryl group, more preferably a $C_1$ to $C_4$ alkyl group, in particular methyl, and $R_2$ and $R_3$ are alkyl groups, more preferably $C_1$ to $C_4$ alkyl groups, in particular ethyl.

The reaction of the compound according to formula (III) with the reducing agent may be carried out in usual organic solvents and at usual temperatures. Preferably alcohols or alcohol/water mixtures are used as suitable solvents. Particularly, an ethanol/water mixture is used. Usually the reaction is carried out at temperatures between −80° C. and 50° C., preferably between −10° C. and 20° C. The reaction time may vary from 10 minutes to 10 hours. Usually, the reaction product (II) is obtained in crystalline form.

In a preferred embodiment a chemoselective reducing agent is used. In this context the term "chemoselective" refers to a reducing agent being capable of reducing the ester groups but not the amido group of the compound according to formula (III).

Examples of suitable reducing agents are $NaBH_4$, $LiBH_4$, $KBH_4$, $NaCNBH_3$, $Na(AcO)_3BH$, L-Selectride®, K-Selectride®, N-Selectride®, benzyltriethylammonium borohydride, lithium dimethylaminoborohydride, lithium morpholinoborohydride, lithium pyrrolidinoborohydride, lithium triethylborohydride, potassium triethylborohydride, potassium triphenylborohydride, benzyltriphenylphosphonium borohydride, sodium triethylborohydride, sodium trimethoxyborohydride, tetrabutylammonium borohydride, tetrabutylammonium cyanoborohydride, tetramethylammonium borohydride, tetramethylammonium triacetoxyborohydride.

Preferably $NaBH_4$ is used as chemoselective reducing agent.

In a preferred embodiment the chemoselective reducing agent is used together with a reduction enhancer. In this context the term "reduction enhancer" refers to a compound being capable of enforcing the reduction force of the reducing agent.

Preferably metal salts are used as reduction enhancer, preferably halides and pseudohalides of metals, more preferably salts selected from $LiCl$, $CaCl_2$, $AlCl_3$, $LaCl_3$, $MnCl_2$, $CoCl_2$ and $ZnCl_2$, most preferably calcium salts are used. In particular, $CaCl_2$ is used as reduction enhancer.

A preferred reaction scheme of the process of the present invention is illustrated below:

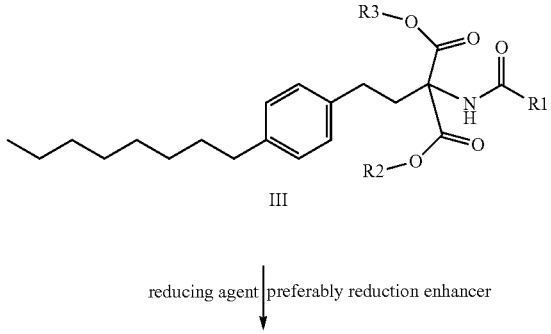

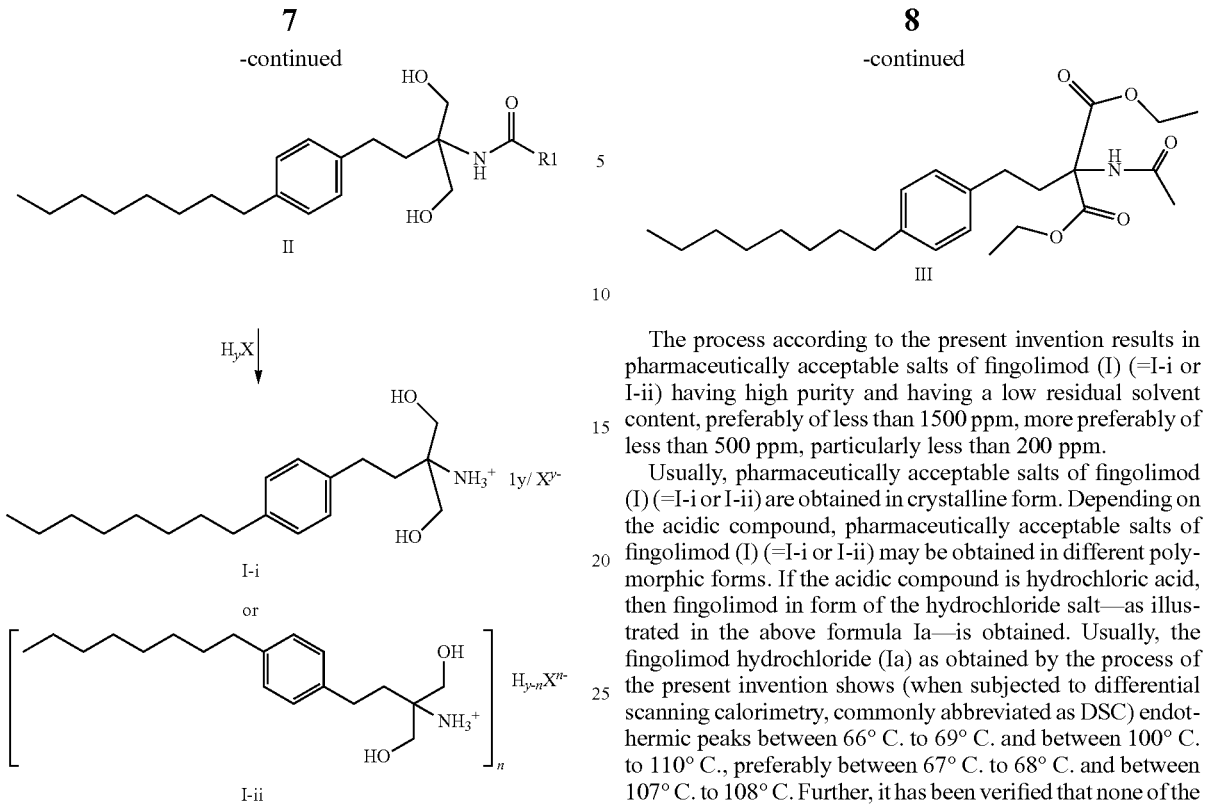

As illustrated in the above scheme, the process of the present invention enables the production of a variety of pharmaceutically acceptable fingolimod salts, wherein in said process the free base of fingolimod does not occur as intermediate product. It has been unexpectedly found that the avoidance of the free base of fingolimod results in a desirable increase of purity and yield.

In addition, it has been found that the above-mentioned objects could be specifically solved by use of a chemoselective reducing agent in a process that avoids the free base of fingolimod as intermediate product. Consequently, a further subject of the present invention is the use of a chemoselective reducing agent in a process for producing a pharmaceutically acceptable salt of fingolimod, wherein fingolimod in form of the free base does not occur as an intermediate in said process.

The preparation of compound III is known in the art. Preferably, compound III is prepared by the following reaction route:

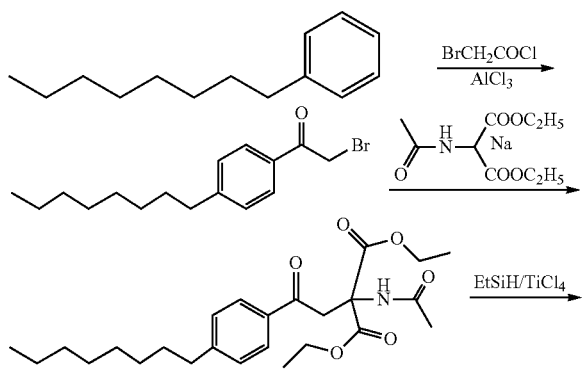

The process according to the present invention results in pharmaceutically acceptable salts of fingolimod (I) (=I-i or I-ii) having high purity and having a low residual solvent content, preferably of less than 1500 ppm, more preferably of less than 500 ppm, particularly less than 200 ppm.

Usually, pharmaceutically acceptable salts of fingolimod (I) (=I-i or I-ii) are obtained in crystalline form. Depending on the acidic compound, pharmaceutically acceptable salts of fingolimod (I) (=I-i or I-ii) may be obtained in different polymorphic forms. If the acidic compound is hydrochloric acid, then fingolimod in form of the hydrochloride salt—as illustrated in the above formula Ia—is obtained. Usually, the fingolimod hydrochloride (Ia) as obtained by the process of the present invention shows (when subjected to differential scanning calorimetry, commonly abbreviated as DSC) endothermic peaks between 66° C. to 69° C. and between 100° C. to 110° C., preferably between 67° C. to 68° C. and between 107° C. to 108° C. Further, it has been verified that none of the two peaks is related to residual solvents or other impurities. Hence, it is assumed that the fingolimod hydrochloride (Ia) as obtained by the process of the present invention crystallizes in a mixture of two polymorphic forms (referred to as mixture of polymorphic forms A and B).

In the present application DSC measurements have been carried out as follows:

DSC thermograms were obtained by using a Mettler® Toledo Model DSC 822$^e$, heating range: 30° C. to 300° C., heating rate: 10° C./min, purge gas: Nitrogen 50 ml/min, sample holder: 40 µl aluminum crucible.

XRD: Samples were analyzed on a Bruker®-AXS D8 Advance powder X-Ray diffractometer. The measurement conditions were as follows:
Detector: VANTEC-13° 2
Radiation: Cu K$\alpha$1(1.5406 A)
Monochromator: None
Second β filter: Ni 0.1 mm
Start angle: 2°
End Angle: 55°
Measurement time: 11 mi
Step: 0.016° 2(–)
Software: EVA (Brukar-AXS, Karlsruhe)

It further has been found that the mixture of polymorphic forms A and B can be converted into pure polymorphic form B. Polymorphic Form B of fingolimod hydrochloride (Ia) unexpectedly shows desirable properties. For example, polymorphic form B shows a constant dissolution profile before and after storage, i.e. the dissolution profile essentially remains constant during shelf life. Furthermore, polymorphic form B shows an advantageous processability in the preparation of pharmaceutical formulations. In particular, the flowability of polymorphic form B is superior when compared to form A or mixtures of forms A and B.

Polymorphic Form B of fingolimod hydrochloride (Ia) shows (when subjected to differential scanning calorimetry) an endothermic peak between 100° C. to 110° C., preferably between 107° C. to 108° C. Thus, a further subject of the present invention is a compound according to formula (Ia) in crystalline form, wherein the differential scanning calorimetry (DSC) shows an endothermic peak between 100° C. to 110° C. but not an endothermic peak between 66° C. to 69° C.

Polymorphic form B of fingolimod hydrochloride (Ia) can be prepared by dissolving the mixture of polymorphic forms A and B (preferably as obtained by the process of the present invention) in a solvent and subsequently subjecting the resulting solution to a rapid drying process. Preferably water, alcohols or alcohol/water mixtures are used as suitable solvents. Particularly water is used. The resulting solution is "rapidly" dried, for example by spray-drying or freeze-drying. Freeze-drying is preferred.

In a preferred embodiment polymorphic form B of fingolimod hydrochloride (Ia) can also be prepared by grinding the mixture of polymorphic forms A and B (preferably as obtained by the process of the present invention). Suitable grinding machines are ball mill, rod mill, mortar and pestle, pebble mill, colloid mill, conical mill or disk mill. Preferred grinding machine is a ball mill from agate or stainless steel, preferably with 10 mm agate round balls.

Hence, a subject of the present invention is a process for producing polymorph B (i.e. the compound of claim 13), comprising
(a) providing polymorph A or a mixture of polymorphs A and B, that means providing a compound according to formula (Ia), wherein the differential scanning calorimetry (DSC) either shows one endothermic peak between 66° C. to 69° C. or two endothermic peaks between 100° C. to 110° C. and 66° C. to 69° C., respectively; and
(b) grinding the material provided in step (a).

It was unexpectedly found that specific milling frequencies might positively affect the purity of form B. Suitable frequencies are between 10 Hz to 100 Hz, preferably between 20 Hz to 50 Hz, most preferably about 30 Hz.

The milling time usually ranges from 5 minutes to 5 hours, preferably from 10 minutes to 4 hours, more preferably from 20 minutes to 3 hours, still more preferably from 30 minutes to 2 hours.

Conversion of a mixture of polymorphic forms A and B to pure polymorphic form B by the above described grinding process particularly affects the flowability properties in a positive way. The resulting product usually has a superior bulk density when compared to polymorphic form B as obtained by freeze-drying.

In the present invention fingolimod is not only provided in form of the hydrochloride. In addition, fingolimod is provided in form of a variety of acid-addition salts. As mentioned above, a further subject of the present invention is fingolimod in form of an acid-addition salt, selected from ascorbate, succinate, oxalate, phosphate, mandelate, adipate, bromide, sulfate, acetate, fumarate, maleate, methane-sulfonate, benzene-sulfonate, L-malate, ethanesulfonate, naphthalene-1,5-disulfonate, naphthalene-1-sulfonate, naphthalene-2-sulfonate, L-aspartate, 4-acetamidobenzoate, (+) camphorate, (+) camphor-10-sulfonate, decanoate, hexanoate, octanoate, cinnamate, dodecylsulfate, ethane-1,2-disulfonate, 2-hydroxyethanesulfonate, glutarate, DL-lactate, 1-hydroxy-2-naphthoate, laureate, salicylate, tartrate, mesylate (methanesulfonate), citrate, benzoate or mixtures thereof.

If in the formula (I-ii) X is succinate, fumarate or malate (D-malate, L-malate, DL-malate, preferably L-malate), then n is preferably 2. If in the formula (I-ii) X is oxalate, phosphate, adipate, citrate or sulfate, then n is preferably 1.

It has been unexpectedly found that the above-mentioned fingolimod salts show advantageous processability in the preparation of pharmaceutical formulations (when being compared to fingolimod hydrochloride, particularly fingolimod hydrochloride in form of a mixture of polymorphic forms A and B). In particular, processability under elevated temperature conditions is significantly improved.

The fingolimod hydrochloride (preferably in form B) or the other above mentioned fingolimod salts preferably are present in particulate form. Usually the particles have a volume mean particle size ($D_{50}$) of 1 to 250 µm, preferably of 2 to 200 µm, more preferably of 5 to 150 µm, further more preferably of 10 to 120 µm, most preferably of 15 to 90 µm. The fingolimod salts preferably possess Hausner ratios in the range of 1.01 to 1.5 or 1.05 to 1.4, preferably of 1.06 to 1.3, more preferably between 1.08 to 1.25. The Hausner ratio is the ratio of tapped density to bulk density, determined according to Ph.Eur. 4.0, 2.9.15.

Within this application, the volume mean particle size ($D_{50}$) is determined by the light scattering method, using a Mastersizer 2000 apparatus made by Malvern Instruments (wet measurement, 2000 rpm, ultrasonic waves for 60 sec., data interpretation via Fraunhofer method).

Finally, for the sake of completeness it is noted that the compounds according to formula (I) (=I-i or I-ii) can be prepared by two alternative routes, which are outlined below.

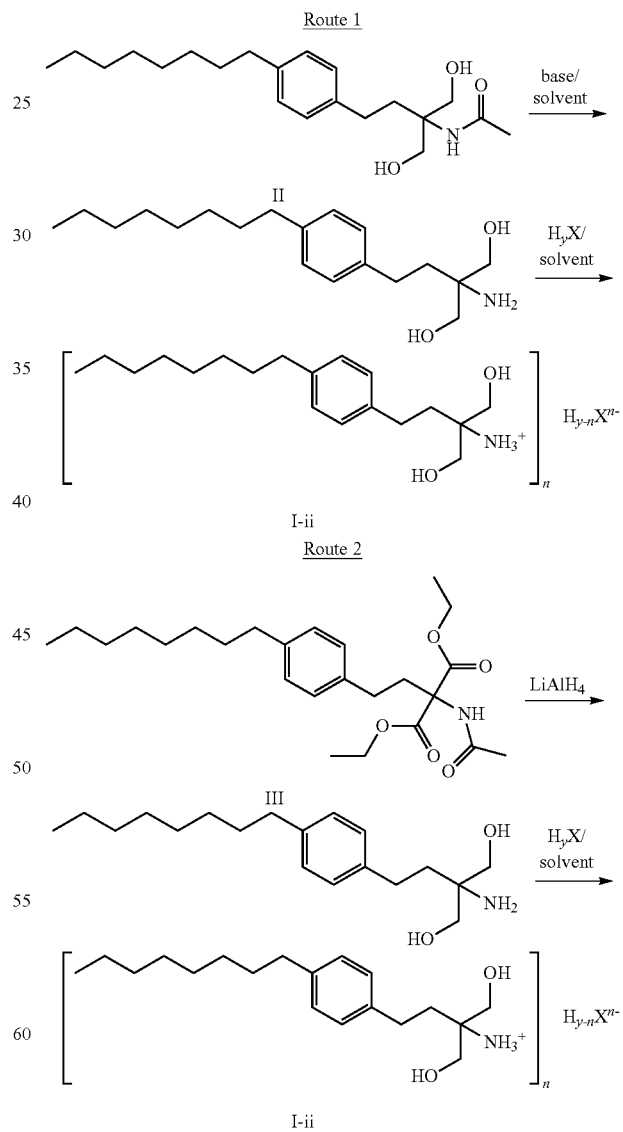

More specific embodiments of Routes 1 and 2 concerning the hydrochloride salt are outlined below.

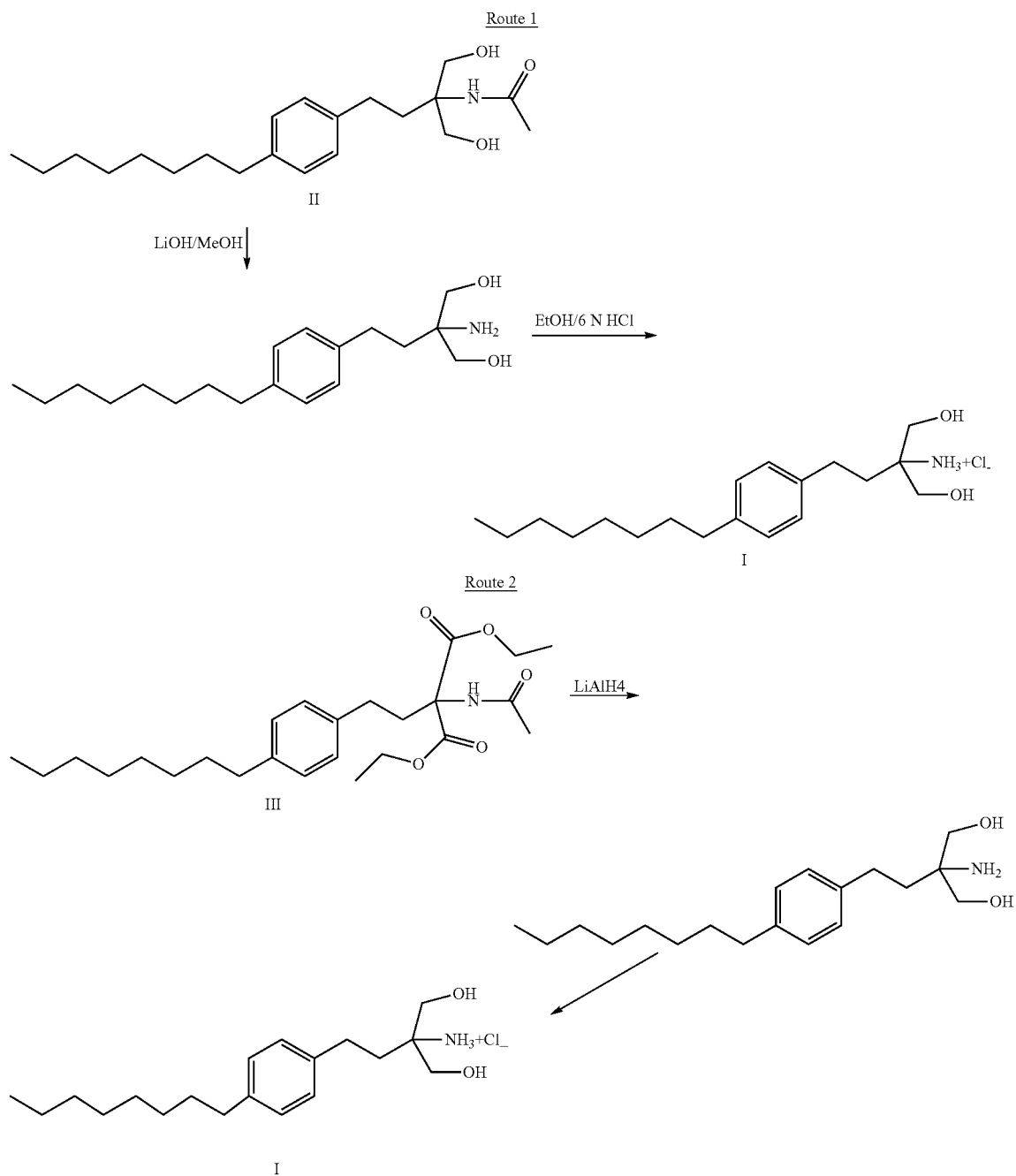

The present invention is illustrated by the following examples.

EXAMPLES

Example 1

Preparation of N-[1,1-bis hydroxymethyl-3-(4-octyl phenyl)-propyl]-acetamide (=Compound According to Formula II)

28 g (64.57 mmole) 2-(acetylamino)-2-[2(4-octylphenyl) ethyl]propanedioic acid diethylester (=compound according to formula (III)) was added to 450 ml ethanol. A solution of 17.91 g calcium chloride in 125 ml water was added in one lot. 12.21 g (322.7 mmole) sodium borohydride was added to the reaction mixture at 0° C. in 1 hr 20 min. The reaction mixture was left overnight for stirring. 100 ml of 1 N HCl was added to neutralize the reaction mixture and inorganic solids were filtered and washed with 200 ml ethanol. Filtrate was evaporated under vacuum. 300 ml water was added to the residue obtained and was extracted with 2×250 ml EtOAC. The organic extract was washed with brine, dried over sodium sulphate and evaporated to give 23 g semisolid.

300 ml petrolether was added to the semisolid obtained and filtered and dried.

Crop 1=8.3 gm

From the filtrate, crop 2 was isolated as an oil.

Crop 1=8.3 gm
Crop 2=13.3 gm. Total yield=95%
IR (cm$^{-1}$): 3283.47, 3096.67, 2957.98, 2925.22, 2871.63, 1624.63, 1560.18.

Example 2

Preparation of Fingolimod Hydrochloride (Ia), Procedure 1

4 ml ethanol was added to 0.75 gm of N-acetyl-fingolimod. To the clear solution obtained 2.7 ml of 6 M HCl was added and the reaction was refluxed for 2 hours. Solvent and water were evaporated on a rotary evaporator to give 0.48 gm of crystalline fingolimod hydrochloride.
IR (cm$^{-1}$): 3268.3, 3034.9, 2923.7, 2853, 1600.8, 1516.1, 1466.8, 1455.9
Residual solvents: Not detected
DSC shows endothermic peaks at 68.6° C. and 100.77° C., indicating a mixture of polymorphic forms A and B.
An X-ray powder diffraction (XRPD) of the resulting fingolimod hydrochloride is shown in FIG. 1.
100 mg was recrystallized from ethanol. DSC shows endothermic peaks at 67.16° C. and 107.6° C. The respective graph is shown in FIG. 2.

Example 3

Preparation of Fingolimod hydrochloride (Ia), Procedure 2

1 ml of concentrated HCl+2 ml water was added to 484 mg (1.38 mmole) N-acetyl-fingolimod (II). The solution was heated at 50° C. to 60° C. for 1 hr 15 min. Toluene was added to the reaction and water was distilled out azeotropically. The residue was triturated with dry diethyl ether and the solid obtained was filtered and dried under vacuum.
Yield=363 mg fingolimod hydrochloride (76.5% yield)
DSC shows two endothermic peaks at 66.18° C. and 108.09° C., indicating a mixture of polymorphic forms A and B.
IR (cm$^{-1}$): 3268.1, 2992.7, 2852, 1601.2, 1516.2, 1469, 1456.2
Residual solvents: Not detected.

Example 4

Freeze-Drying 500 mg of fingolimod hydrochloride, obtainable by Example 2, was dissolved in 2.3 ml water. It was frozen to a thin film in a flask by using liquid nitrogen and was connected to a Freeze dryer.
A fluffy solid was obtained. Yield=496 mg
DSC shows a peak at 107.45° C., whereas no peak was observed at about 66° C., indicating the presence of polymorphic form B only.
IR (cm$^{-1}$): 3267.6, 2922.9, 1601.1, 1516.8, 1469.1, 1456.5, 1069.3
XRD shows characteristic peaks at 2θ=3.5°, 7.1°, 10.6°, 20.2°, 20.4°, 21.4°.
See FIGS. 3 and 4.

Example 5

Preparation of Fingolimod hydrochloride (Ia), Procedure 3

500 mg (2.14 mmole) N-acetyl-fingolimod (II)+4 ml ethanol+2 ml 6 N HCl. Solution was refluxed for 1.5 hours. Ethanol was removed under vacuum. The remaining mixture was frozen in liquid nitrogen and connected to a freeze dryer. 350 mg solid was obtained.
DSC shows a major endothermic peak at 104.75° C.

Example 6

Milling of Fingolimod HCl 200 mg of Fingolimod HCl: DSC shows 2 peaks at 66.8 (−20 J/g) and 108.9° C. (−117.6 J/g), was milled at 30 Hz for 1 hour, using 10 ml agate jar and 10 mm agate balls.
Yield=194 mg
DSC shows endothermic peak at 109.72° C.
See FIGS. 5 and 6.

Example 7

Preparation of Fingolimod hydrobromide 4 ml ethanol was added to 500 mg (2.14 mmole) of N-acetyl-fingolimod. 2 ml 47% aq HBr was added to the clear solution and was refluxed for 2 hours. The solvent was evaporated under vacuum and the obtained residue was treated with 50 ml diethyl ether, and the mixture was stirred for 1 hour. Solid was filtered and dried at 40° C. under vacuum.
Yield=488 mg.
DSC shows an endotherm at 83.4° C.
See FIGS. 7 and 8.

Example 8

Fingolimod salts ascorbate, succinate, oxalate, phosphate, mandelate, adipate, sulfate, malate, malate hydrate, acetate, benzoate, citrate, fumarate, maleate and mesylate were prepared in a previously described way.
See FIGS. 9-23.

Fingolimod succinate

Yield=0.266 g
DSC shows a major endotherm at 152.68° C. and a minor endotherm at 183.28° C.
Melting point=151.6-153.1° C.
HPLC purity=99.39%
IR: 3255, 2926.7, 2853.9, 1652.5, 1618.6, 1541.6, 1513.2 cm$^{-1}$
Characteristic XRPD-peaks at 2θ=3.2°, 9.8°, 19.8°, 23.2°, 26.1°, 33.2°.
According to formula (I-ii), y and n are 2.

Fingolimod oxalate

Yield=0.288 g
DSC shows overlapping endotherms at 166.20 and 169.31° C.
Melting point=162.6-167.7° C.
HPLC purity=99.3%
IR: 3374.1, 2955.4, 2852.2, 1721.3, 1698.6, 1618.9 cm$^{-1}$
Characteristic XRPD-peaks at 2θ=2.8°, 3.1°, 4.5°, 9.0°, 18.1°, 20.4°, 22.6°, 27.2°.
According to formula (I-ii), y is 2 and n is 1.

Fingolimod phosphate

Yield=0.312 g
DSC shows endotherms at 41.10, 72.13, 129.37 and 170.36° C.
Melting point=167.1-174.9° C.
HPLC purity=99.2%
IR: 3386.8, 2923.6, 2850.7, 1655.6, 1633.9 cm$^{-1}$
Characteristic XRPD-peaks at 2θ=2.9°, 8.7°, 18.9°, 22.4°, 22.9°.
According to formula (I-ii), y is 3 and n is 1.

Fingolimod mandelate

Yield=0.218 g
DSC shows a major endotherm at 126.46° C. and a minor endotherm at 168.94° C.
Melting point=126.3-131.2° C.
HPLC purity=99.8%
IR: 3464.9, 2922.3, 2852.7, 1634.4, 1613.7, 1575.3 cm$^{-1}$
Characteristic XRPD-peaks at 2θ=4.4°, 8.8°, 17.8°, 18.7°, 20.8°, 22.1°, 26.8°, 31.3°.

Fingolimod adipate

Yield=0.271 g
DSC shows a minor endotherm at 95.50, a major endotherm at 121.67 and a minor endotherm at 165.47° C.
Melting point=120.4-121.7° C.
HPLC purity=99.55%
IR: 3332.9, 2925.9, 2871.7, 1605.5, 1558, 1527.6 cm$^{-1}$
Characteristic XRPD-peaks at 2θ=2.3°, 3.4°, 10.4°, 17.4°, 18.5°, 21.5°, 28.5°, 33.9°, 37.2°.
According to formula (I-ii), y is 2 and n is 1.

Fingolimod ascorbate

Yield=0.255 g
DSC does not show any endothermic peak indicating amorphous nature.
HPLC purity=99.06%
IR: 2924.4, 2853.7, 1721, 1607 cm$^{-1}$.

Fingolimod sulfate

Two different products were obtained from precipitation and from crystallization out of mother liquor. Both were analyzed separately.
Product I (precipitate):
Yield=0.124 g
Characteristic XRPD-peaks at 2θ=2.8°, 8.5°, 17.1°, 25.8°.
Product II (obtained from mother liquor):
The mother liquor on keeping for 30 min at room temperature gave more precipitate, which was filtered and dried at 40° C. under vacuum for 1 h to obtain a white solid.
Yield=0.077 g
Characteristic XRPD-peaks at 2θ=2.8°, 3.0°, 6.2°, 8.5°, 17.1°, 19.6°, 21.4°, 23.2°.
According to formula (I-ii), y is 2 and n is 1.

Fingolimod malate

Yield=86.2%
DSC showed a sharp endotherm at 155.64° C.
IR: 3237, 2925.9, 2853.8, 1642.6, 1561, 1514.8, 1467.1, 1390.7 cm$^{-1}$
Melting point=150.9-153° C.
HPLC purity=99.7%
Characteristic XRPD-peaks at 2θ=3.12, 6.19, 9.35, 18.35, 18.71, 21.91, 22.31, 24.99, 31.38.
According to formula (I-ii) y is 2 and n is 2.

Fingolimod malate hydrate

DSC showed two small endotherms at 59.6 and 69.47 and a sharp endotherm at 151.24° C.
Melting point=152.3-159.6° C.
IR: 3371.3, 2925.4, 2853.2, 1628.5, 1551.4 cm$^{-1}$
HPLC purity=99.78%
Water content: 4.7702%
Characteristic XRPD-peaks at 2θ=3.02, 9.19, 11.25, 18.50, 19.79, 20.85, 22.08, 22.69, 24.71, 25.18, 28.50, 28.65, 31.15.
According to formula (I-ii) y is 2 and n is 2.

Fingolimod Free Base

Yield=73.1%
DSC showed a sharp endotherm at 124.2° C.
HPLC purity=98.91%
IR: 3353.3, 3324.98, 3290.98, 2925.2, 2853.9, 1573, 1465.9, 1018.7 cm$^{-1}$
Characteristic XRPD-peaks at 2θ=19.42, 20.71, 23.37, 27.35, 30.4, 31.36, 35.4.

Fingolimod acetate

Yield=88.16%
DSC showed an endotherm at 147.92° C.
Melting point: 150.1-152.1° C.
IR: 3229.3, 3134.2, 3018.1, 2923.0, 2851.8, 1630.8, 1556.5, 1513.3 cm$^{-1}$
HPLC purity=99.48%
Characteristic XRD-peaks at 2θ=4.99, 8.51, 10.09, 15.20, 19.28, 20.06, 21.48, 21.95, 25.22, 25.53, 30.78, 36.08.

Fingolimod benzoate

Yield=97.8%
DSC shows an endotherm at 164.49° C.
Melting point=165.9-168° C.
HPLC purity=99.9%
IR: 3280.5, 3090.1, 2957.4, 2923.2, 2851.8, 1646.1, 1618.8, 1592 cm$^{-1}$
Characteristic XRD-peaks at 2θ=3.80, 7.7, 15.42, 19.30, 19.70, 20.04, 21.76.

Fingolimod citrate

Yield=77%
DSC showed endotherms at 56.29, 61.27, 129.61, 132.77, 167.97° C.
Melting point: 168-169.7° C.
IR: 3340.6, 3228.3, 2923.4, 1602.4, 1571.0 cm$^{-1}$
HPLC purity=99.16%
Characteristic XRD peaks at 2θ=2.56, 7.71, 10.31, 12.92, 15.67, 15.88, 17.50, 17.85, 22.67, 28.41, 29.47.
According to formula (I-ii), y is 3 and n is 1.

Fingolimod fumarate

Yield=85%
DSC showed small endotherms at 50.46, 175.69 and a sharp endotherm at 199.56, followed by a merging endotherm at 200.75° C.

Melting point=192-193.4° C.
HPLC purity=99.58%
IR: 3354.0, 2870.5, 2650.4, 1644.2, 1626.5, 1587.9, 1521.7 cm$^{-1}$
According to formula (I-ii), y is 2 and n is 2.

The invention claimed is:
1. A crystalline form of a compound according to formula (I-ii)

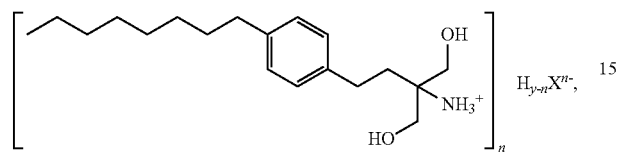

wherein X is citrate, y is 3 and n is 1;
characterized by
i) differential scanning calorimetry (DSC) showing endothermic peaks at 56.29, 61.27, 129.61, 132.77 and 167.97° C.; and/or
ii) a melting point of 168-169.7° C.;
iii) IR peaks at 3340.6, 3228.3, 2923.4, 1602.4, and 1571.9 cm$^{-1}$;
iv) XRD peaks at 2.56, 7.71, 10.31, 12.92, 15.67, 15.88, 17.50, 17.85, 22.67, 28.41 and 29.47 degrees 2θ; or a combination thereof.

2. A process for producing the compound of formula (I-ii)

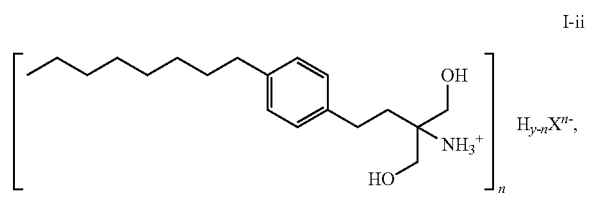

wherein X is citrate, y is 3 and n is 1
comprising reacting a compound according to formula (II)

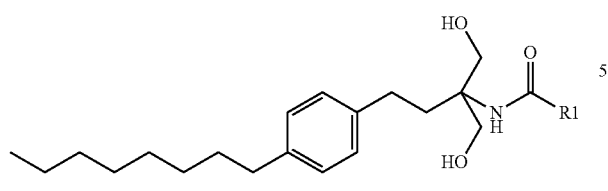

with an acidic compound of the formula $H_yX$, wherein the acidic compound is citric acid and H is a dissociable hydrogen atom,
wherein y is 3, n is 1, and $R_1$ is an organic residue.

3. The process according to claim 2, wherein $R_1$ is an alkyl or aryl group.
4. The process according to claim 3, wherein $R_1$ is methyl.
5. The process according to claim 2, wherein the compound according to formula (I-ii) is dissolved and subsequently freeze-dried.
6. The process according to claim 2, wherein the compound according to formula (II)

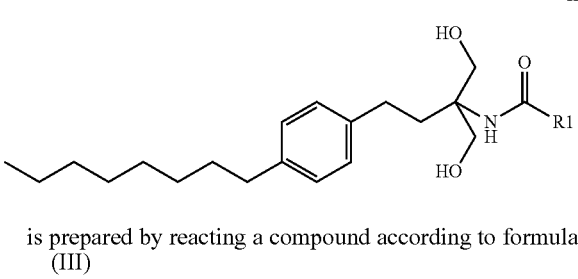

is prepared by reacting a compound according to formula (III)

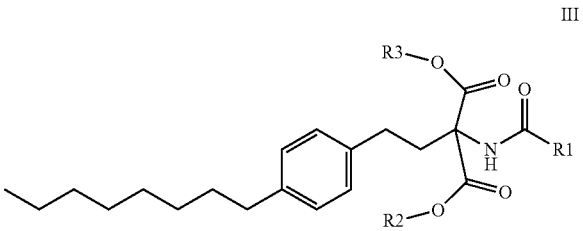

with a reducing agent,
wherein $R_1$ is an alkyl or aryl group, and $R_2$ and $R_3$ are alkyl groups.

7. The process according to claim 6, wherein $R_1$ is methyl, and $R_2$ and $R_3$ are ethyl.
8. The process according to claim 5, wherein the compound according to formula (II)

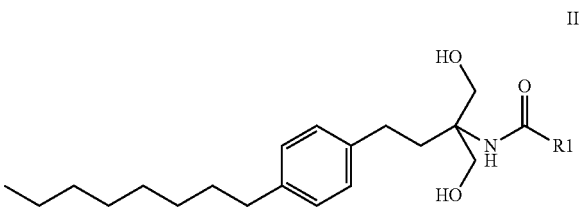

is prepared by reacting a compound according to formula (III)

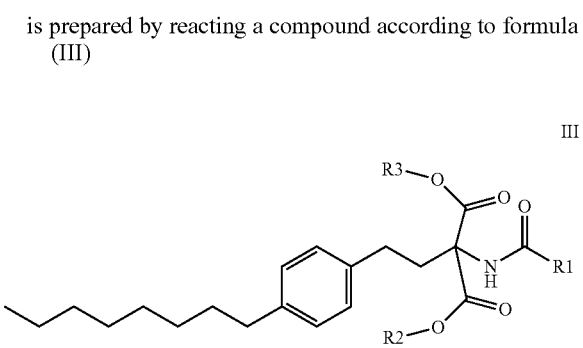

with a reducing agent,
wherein $R_1$ is an alkyl or aryl group, and $R_2$ and $R_3$ are alkyl groups.

9. The process according to claim 8, wherein $R_1$ is methyl, and $R_2$ and $R_3$ are ethyl.
10. The process according to claim 6, wherein the reducing agent is a chemoselective reducing agent.
11. The process according to claim 10, wherein the chemoselective reducing agent is $NaBH_4$.
12. The process according to claim 8, wherein the reducing agent is a chemoselective reducing agent.

13. The process according to claim 12, wherein the chemoselective reducing agent is $NaBH_4$.

14. The process according to claim 6, further comprising addition of a reduction enhancer.

15. The process according to claim 14, wherein the reduction enhancer is $CaCl_2$.

16. A pharmaceutical formulation, comprising the crystalline form of the compound according to claim 1.

17. A method for the treatment of relapsing-remitting multiple sclerosis in a subject, comprising administering the crystalline form of the compound according to claim 1 to the subject.

18. A process for preparing a pharmaceutical formulation comprising combining the compound according to claim 1 with at least one pharmaceutically acceptable excipient.

\* \* \* \* \*